(12) United States Patent
Spaete et al.

(10) Patent No.: US 6,190,860 B1
(45) Date of Patent: Feb. 20, 2001

(54) METHOD TO DETECT CMV BY HYBRIDIZATION WITH A GP55 SPECIFIC DNA PROBE

(75) Inventors: Richard R. Spaete, Belmont; Carol A. Pachl, El Cerrito, both of CA (US)

(73) Assignee: Chiron Corporation, Emeryville, CA (US)

(*) Notice: Under 35 U.S.C. 154(b), the term of this patent shall be extended for 0 days.

(21) Appl. No.: 08/448,780

(22) Filed: May 24, 1995

Related U.S. Application Data

(62) Division of application No. 08/341,293, filed on Nov. 15, 1994, now Pat. No. 5,547,834, which is a continuation of application No. 07/671,690, filed on Mar. 26, 1991, now abandoned, which is a continuation-in-part of application No. 07/149,715, filed on Jan. 29, 1988, now abandoned.

(51) Int. Cl.[7] .............................. C12Q 1/70; C12Q 1/68
(52) U.S. Cl. ...................................... 435/5; 435/6
(58) Field of Search .................... 435/6, 5, 77; 536/24.3; 935/78

(56) References Cited

U.S. PATENT DOCUMENTS

| | | | |
|---|---|---|---|
| 4,313,927 | 2/1982 | Fridlender | 435/5 |
| 4,460,689 | 7/1984 | Foor et al. | 435/91.41 |
| 4,554,101 | 11/1985 | Hopp | 530/324 |
| 4,689,225 | 8/1987 | Pereira | 424/230.1 |
| 4,762,780 | * 8/1988 | Spector et al. | 435/6 |
| 5,043,281 | 8/1991 | Masuho et al. | 435/69.4 |
| 5,075,213 | * 12/1991 | Pande et al. | 435/5 |
| 5,124,440 | * 6/1992 | Gehrz et al. | 530/395 |
| 5,126,130 | 6/1992 | Lussenhop et al. | 424/147.1 |
| 5,173,402 | * 12/1992 | Spector et al. | 435/6 |
| 5,262,297 | * 11/1993 | Sutton | 435/5 |
| 5,403,711 | * 4/1995 | Walder et al. | 435/6 |
| 5,407,795 | * 4/1995 | Kolberg et al. | 435/5 |

FOREIGN PATENT DOCUMENTS

| | | |
|---|---|---|
| 0 174 444 | 3/1986 | (EP) . |
| 0 180 288 | 9/1986 | (EP) . |
| WO 85/05123 | 11/1985 | (WO) . |
| WO 87/05326 | 9/1987 | (WO) . |

OTHER PUBLICATIONS

Britt et al., *J. Virol.* (1986) 58(1):185–191.
Britt, *Virology* (1984) 135:369–378.
Cranage et al., *EMBO J.* (1986) 5(11):3057–3063.
Darnell et al., Eds., "Molecular Cell Biology" (1986) Scientific American Books, Inc., W.H. Freeman and Company Publishers, New York, pp. 954–957.
Gonczol et al., *J. Virol.* (1986) 58(2):661–664.
Law et al., *J. Med. Virol.* (1985) 17:155–166.
Mach et al., *J. Gen. Virol.* (1986) 67:1461–1467.
Meyer et al., *J. Virol.* (1988) 62:(7):2243–2250.
Nowak et al., *Virology* (1984) 132:325–338.
Pereira et al., *Virology* (1984) 139:73–86.
Pereira et al., *Infection & Immunity* (1982) 36(3):933–942.
Quinnan et al., *Annals of Internal Medicine* (1984) 101:478–483.
Rasmussen et al., *J. Virol.* (1985) 55(2):274–280.
Rasmussen et al., *Proc. Natl. Acad. Sci.* (1984) 81:876–880.
Rider et al., 12th International Herpesvirus Workshop Jul. 30–Aug. 4, 1987, p. 148.
Southern et al., *J. Mol. Biol.*, (1975) 98:503–517.
Spaete et al., *Virology* (1988) 167(1):207–255.
Spaete et al., 12th International Herpesvirus Workshop Jul. 30–Aug. 4, 1987, p. 165.
Stannard et al., 12th Intrnational Herpesvirus Workshop Jul. 30–Aug. 4, 1987, p. 112.
Stinski et al., *J. Virol.* (1976) 19(2):594–609.
Cranage et al. (1986) *EMBO Journal* 5:3057–63.*
Chou (1992) *Virology* 188:388–90.*
Olive et al. (1989) *Journal of Medical Virology* 29:232–237.*
Rogers et al. (1990) *Amer. J. Pathology* 136:541–48.*
Chou and Merigan (1983) *New England J Medicine* 308:921–25.*

* cited by examiner

*Primary Examiner*—Lisa B. Arthur
(74) *Attorney, Agent, or Firm*—McDonnell Boehnen Hulbert & Berghoff; Michael S. Greenfield

(57) ABSTRACT

The present invention provides recombinant polypeptides derived from CMV glycoprotein gB and truncated fragments thereof which contain at least one epitope which is immunologically identifiable with one encoded by the CMV genome. The complete characterization of the gB protein, including the identity of glycoprotein gp55, permits the production of polypeptides which are useful as standards or reagents in diagnostic tests and/or as components of vaccines. This invention provides recombinant polypeptides and recombinant polynucleotides encoding these polypeptides wherein a neutralizing epitope of gB is localized within gp55.

3 Claims, 16 Drawing Sheets

```
                                                                               TOWNE
                                                                               AD169
-949  CTGCAGAAGGTTTCGGAGGTGGGCTATGGCAAGGTGATCCGTTGCATCAAAACGCAGGA
      CTGCAGAAGGTCTCGGAGGTGGGCTATGGCAAGGTGATCCGTTGCATCAAAACGCAGGA

GCGTCTGACTAGCAAACTCATGATGTCAACCTAGTGGGCCCTTGTGTCTGACTTTAT
      GCGTCTGACTAGCAAGCTCATGATGTCAATCTAGTGGGCCCTTGTGTCTGACTTTAT

-830  CTCTAAGCTCATGAATGGGTTTCTATACCGCAGCCAATACCACCAGGACCAAGACGTGG
      CTCTAAGCTCATGAATGGGTTTCTGTACCGCAGCCAATACCACCAGGACCAAGACGTGG

TGGACGTGGGGGATCAGTTCACGTACGATGAGCACCTGTATGTGTCAATAACCTGATCC
      TGGACGTGGGGTGATCAGTTCACCTACGATGAGCACCTGTATGTGTCAATAACCTGATCC

-711  ACAAGAGTCTGCCTGTGGAATCCCTCCCCGCTACTGGGTCAGCAGATCTACGAGTTGTGT
      ACAAGAGTCTGCCTGTGGAATCCCTCCCCGCTACTGGGTCAGCAGATCTACGAGTTGTGT

AACGGGCCCCTCTTCACACACTGCACCGATCGTATCCCCTCTCACAATGTGGACATG
      AACGGGCCCCCTCTTCACCCACTGCACCGATCGTTATCCCCTCTCACAATGTGGACATG

-592  GCCTATGCCTGCGACAACGGGCGGCGTACTACCCCACGTCAAGGACGATTGGTCAAATG
      GCCTATGCCTGCGACAACGGGCGGCGTACTACCCCACGTCAAGGACGATTGGTCAAATG

CGCGGAAGGTACCGTGTATCCCAGTGAGTGGTGTGAAGTACATGGTTTTTCAA
      CGCGGAAGGTACCGTGTATCCCAGTGAGTGGTGTGAAGTATATGGGTTTTTCAA

-473  TTTTTCGGACTGTCAGGATCTAAACGTGCTGCAGAAGGAGATGTGATGCACGTGCGGG
      TTTTTCGGACTGTCAGGACCTAAACGTGCTGCAGAAGGAGATGTGATGCACGTGCGGG

AGCTCGTGCTCTCCGTCGCACTATATAATGAAACTTTCGGAAACAACTCTCGATCGCGT
      AGCTCGTGCTCTCCGTCGCACTATATAATGAAACTTTCGGAAACAACTCTCGATCGCGT
```

FIG. 2A

```
-354  GCCTGCGCGACGAACTGCACCCGGACAGAGATGTGATTCTCACGTATAACAAAGAGTGG
      GCCTGCGCGACGAACTGCACCCGGACAGAGATGTGATTCTCACGTATAACAAAGAGTGG

CCGCTGCTGCTTCGTCACGAAGGAAGTCTTTATAAGTCCAAAGATCTATATCTCCTCCTC
      CCGCTGCTGCTTCGTCACGAAGGAAGTCTTTATAAGTCCAAAGATCTATATCTCCTCCTC

-235  TACAGGCATCTGTCCAGACCGGATGAGAGTGGCGACGTGCCAACAGCTCCCGGCCAA
      TACAGGCATCTGTCCAGACCGGATGAGAGTGGCGACGTGCCAACAGCTCCCGGCCAA

GCCCTCCACCCTGACGGCCGCGGGCCCGTCTCGGGTGCCTTCAGGGAGCCGGACCGACC
      GCCCTCCACCCTGACGGCCGCGGGCCCGTCTCGGGTGTCTTCAGGGAGCCGGACCGACC

-116  TTGGCTGCCAAGTCCGTACCCCTCCCTCGACCGCGGGCGTTCCCGGAGGGTCCGCG
      TTGGCTGCCAAGTCCGTATTTTTCCCTCGACTGCGGGGTGTTTCCCGGAGGGTCCGCG

CAACACGCAAGAGACCACGAGCGCCTCATCGCTGCTGGATTTGGCCCGCGACGAAC
      CGACACGCAAGAGACCACGAGCGCCTCATCGCTGCTGGATTTGGCCCGCGACGAAC
    1                                                          10
      Met Glu Ser Arg Ile Trp Cys Leu Val Val Cys Val Asn Leu Cys
   1  ATG GAA TCC AGG ATC TGG TGC CTG GTA GTC TGC GTT AAC TTG TGT
      ATG GAA TCC AGG ATC TGG TGC CTG GTA GTC TGC GTT AAC CTG TGT
      Met Glu Ser Arg Ile Trp Cys Leu Val Val Cys Val Asn Leu Cys
                        20
      Ile Val Cys Leu Gly Ala Ala Val Ser Ser Ser Ser Thr        Arg
      ATC GTC TGT CTG GGT GCT GCG GTT TCC TCA TCT TCT ACT  ...   CGT
      ATC GTC TGT CTG GGT GCT GCG GTT TCC TCT AGT ACT TCC CAT
      Ile Val Cys Leu Gly Ala Ala Val Ser Ser Ser Thr Ser His
                                                           29
```

```
                                                                128
355  Glu Asp Leu Asp Glu Gly Ile Met Val Tyr Lys Arg Asn Ile
     GAA GAC CTG GAC GAG GGC ATC ATG GTC TAC AAA CGC AAC ATC
     GAA GAC TTG GAT GAG GGC ATC ATG GTG TAC AAG CGC AAC ATC
     Glu Asp Leu Asp Glu Gly Ile Met Val Tyr Lys Arg Asn Ile
                                                                148
     Val Ala His Thr Phe Lys Val Arg Val Tyr Gln Lys Val Leu Thr
     GTC GCG CAC ACC TTT AAG GTA CGA GTC TAC CAG AAG GTT TTG ACG
     GTG GCG CAC ACC TTT AAG GTA CGG GTC TAC CAA AAG GTT TTG ACG
     Val Ala His Thr Phe Lys Val Arg Val Tyr Gln Lys Val Leu Thr
                                            158
     Phe Arg Ser Tyr Ala Tyr Ile His Thr Tyr Leu Leu Gly
445  TTT CGT AGC TAC GCT TAC ATC CAC ACT TAT CTG CTG GGC
     TTT CGT AGC TAC GCT TAC ATC TAC ACT TAT CTG CTG GGC
     Phe Arg Ser Tyr Ala Tyr Ile Tyr Thr Tyr Leu Leu Gly
                                                                178
     Ser Asn Thr Glu Tyr Val Ala Pro Pro Met Trp Glu Ile His His
     AGC AAC ACG GAA TAC GTG GCG CCT CCT ATG TGG GAG ATT CAT CAT
     AGC AAT ACG GAA TAC GTG GCG CCT CCT ATG TGG GAG ATT CAT CAC
     Ser Asn Thr Glu Tyr Val Ala Pro Pro Met Trp Glu Ile His His
                                       188
     Ile Asn Ser His Ser Gln Cys Tyr Ser Ser Tyr Ser Arg Val Ile
535  ATC AAC AGT CAC AGT CAG TGC TAC AGT TCC TAC AGC CGC GTT ATA
     ATC AAC AAG TTT GCT CAA TGC TAC AGT TCC TAC AGC CGC GTT ATA
     Ile Asn Lys Phe Ala Gln Cys Tyr Ser Ser Tyr Ser Arg Val Ile
                   198                                          208
     Ala Gly Thr Val Phe Val Ala Tyr His Arg Asp Ser Tyr Glu Asn
     GCA GGC ACG GTT TTC GTG GCT TAT CAT AGG GAC AGC TAT GAA AAC
     GGA GGC ACG GTT TTC GTG GCT TAT CAT AGG GAC AGT TAT GAA AAC
     Gly Gly Thr Val Phe Val Ala Tyr His Arg Asp Ser Tyr Glu Asn
```

FIG. 2D

```
      Lys Thr Met Gln Leu Met Pro Asp Asp Tyr Ser Asn Thr His Ser
625   AAA ACC ATG CAA TTA ATG CCC GAC GAT TAT TCC AAC ACC CAC AGT
      AAA ACC ATG CAA TTA ATT CCC GAC GAT TAT TCC AAC ACC CAC AGT
      Lys Thr Met Gln Leu Ile Pro Asp Asp Tyr Ser Asn Thr His Ser
                          228                              238

Thr Arg Tyr Val Thr Val Lys Asp Gln Trp His Ser Arg Gly Ser
      ACC CGT TAC GTG ACG GTC AAG GAT CAA TGG CAC AGC CGC GGC AGC
      ACC CGT TAC GTG ACG GTC AAG GAT CAA TGG CAC AGC CGC GGC AGC
      Thr Arg Tyr Val Thr Val Lys Asp Gln Trp His Ser Arg Gly Ser
                                                         248

Thr Trp Leu Tyr Arg Glu Thr Cys Asn Leu Asn Cys Met Val Thr
715   ACC TGG CTC TAT CGT GAG ACC TGT AAT CTG AAT TGT ATG GTG ACC
      ACC TGG CTC TAT CGT GAG ACC TGT AAT CTG AAT TGT ATG CTG ACC
      Thr Trp Leu Tyr Arg Glu Thr Cys Asn Leu Asn Cys Met Leu Thr
                          258                                  268

Ile Thr Ala Arg Ser Lys Tyr Pro Tyr His Phe Phe Ala Thr
      ATC ACT GCG CGC TCC AAG TAT CCC TAT CAT TTT TTC GCA ACT
      ATC ACT GCG CGC TCC AAG TAT CCT TAT CAT TTT TTT GCA ACT
      Ile Thr Ala Arg Ser Lys Tyr Pro Tyr His Phe Phe Ala Thr
                                              278

Ser Thr Gly Asp Val Val Asp Ile Ser Pro Phe Tyr Asn Gly Thr
805   TCC ACG GGT GAT GTG GTT GAC ATT TCT CCT TTC TAC AAC GGA ACT
      TCC ACG GGT GAT GTG GTT TAC ATT TCT CCT TTC TAC AAC GGA ACC
      Ser Thr Gly Asp Val Val Tyr Ile Ser Pro Phe Tyr Asn Gly Thr
                          *   288                              298

Asn Arg Asn Ala Ser Tyr Phe Gly Glu Asn Ala Asp Lys Phe Phe
      AAT CGC AAT GCC AGC TAT TTT GGA GAA AAC GCC GAC AAG TTT TTC
      AAT CGC AAT GCC AGC TAC TTT GGA GAA AAC GCC GAC AAG TTT TTC
      Asn Arg Asn Ala Ser Tyr Phe Gly Glu Asn Ala Asp Lys Phe Phe
```

FIG. 2E

```
      Ile Phe Pro Asn Tyr Thr Ile Val Ser Asp Phe Gly Arg Pro Asn
895   ATT TTT CCG AAC TAC ACT ATC GTC TCC GAC TTT GGA AGA CCG AAT
      ATT TTC CCG AAC TAC ACC ATC GTT TCC GAC TTT GGA AGA CCC AAC
      Ile Phe Pro Asn Tyr Thr Ile Val Ser Asp Phe Gly Arg Pro Asn
                              *                          308          328

Ser Ala Leu Glu Thr His Arg Leu Val Ala Phe Leu Glu Arg Ala
      TCT GCG TTA GAG ACC CAC AGG TTG GTG GCT TTT CTT GAA CGT GCG
      GCT GCG CCA GAA ACC CAT AGG TTG GTG GCT TTT CTC GAA CGT GCC
      Ala Ala Pro Glu Thr His Arg Leu Val Ala Phe Leu Glu Arg Ala
                                              338

Asp Ser Val Ile Ser Glu Trp Asp Ile Gln Asp Glu Lys Asn Val Thr
985   GAC TCA GTG ATC TCC GAT ATA CAG GAC GAG AAG AAT GTT ACT
      GAC TCG GTG ATC TCT TGG GAT ATA CAG GAC GAG AAG AAT GTC ACC
      Asp Ser Val Ile Ser Trp Asp Ile Gln Asp Glu Lys Asn Val Thr
                                                                 358

Cys Gln Leu Thr Phe Trp Glu Ala Ser Glu Arg Thr Ile Arg Ser
      TGT CAA CTC ACT TTC TGG GAA GCC TCG GAA CGC ACC ATT CGT TCC
      TGC CAG CTC ACC TTC TGG GAA GCC TCG GAA CGT ACT ATC CGT TCC
      Cys Gln Leu Thr Phe Trp Glu Ala Ser Glu Arg Thr Ile Arg Ser
                                              368

Glu Ala Glu Asp Ser Tyr His Phe Ser Ala Lys Met Thr Ala
      GAA GCC GAG GAC TCG TAT CAC TTT TCT GCC AAA ATG ACC GCC
1075  GAA GCC GAA GAC TCG TAC CAC TTT TCT GCC AAA ATG ACT GCA
      Glu Ala Glu Asp Ser Tyr His Phe Ser Ala Lys Met Thr Ala
                              378                 *              388

Thr Phe Leu Ser Lys Lys Gln Glu Val Asn Met Ser Asp Ser Ala
      ACT TTC TTA TCT AAG AAG CAA GAG GTG AAC ATG TCC GAC TCT GCG
      ACT TTT CTG TCT AAG AAA CAA GAA GTG AAC ATG TCC GAC TCC GCG
      Thr Phe Leu Ser Lys Lys Gln Glu Val Asn Met Ser Asp Ser Ala
```

FIG. 2F

```
        Leu Asp Cys Val Arg Asp Glu Ala Ile Asn Lys Leu Gln Gln Ile
1165    CTG GAC TGT GTA CGT GAT GAG GCC ATA AAT AAG TTA CAG CAG ATT
        CTG GAC TGC GTA CGT GAT GAG GCT ATA AAT AAG TTA CAG CAG ATT
        Leu Asp Cys Val Arg Asp Glu Ala Ile Asn Lys Leu Gln Gln Ile
                        *                  408                   *

Phe Asn Thr Ser Tyr Asn Gln Thr Tyr Glu Lys Tyr Gly Asn Val
        TTC AAT ACT TCA TAC AAT CAA ACA TAT GAA AAA TAT GGA AAC GTG
        TTC AAT ACT TCA TAC AAT CAA ACA TAT GAA AAA TAC GGA AAC GTG
        Phe Asn Thr Ser Tyr Asn Gln Thr Tyr Glu Lys Tyr Gly Asn Val

Ser Val Phe Glu Thr Gly Gly Leu Val Val Phe Trp Gln Gly
        TCC GTC TTT GAA ACT GGT GGT TTG GTG GTG TTC TGG CAA GGT
1255    TCC GTC TTC GAA ACC AGC GGC CTG GTG TTC TGG CAA GGC
        Ser Val Phe Glu Thr Ser Gly Leu Val Val Phe Trp Gln Gly
                              438                              *

Ile Lys Gln Lys Ser Leu Ser Leu Val Glu Leu Glu Arg Leu Ala Asn Arg
        ATC AAG CAA AAA TCT CTG GTG GAA CTC GAA CGT TTG GCC AAC CGC
        ATC AAG CAA AAA TCT CTG GTG GAA TTG GAA CGT TTG GCC AAT CGA
        Ile Lys Gln Lys Ser Leu Val Glu Leu Glu Arg Leu Ala Asn Arg
                                                 458                *

Ser Ser Leu Asn Leu Thr His  Asn  Arg Thr  Lys  Arg Ser Thr Asp
        TCC AGT CTG AAT CTT ACT CAT  AAT  AGA ACC  AAA  AGA AGT ACA GAT
1345    TCC AGT CTG AAT ATC ACT CAT  ...  AGG ACC  AGA  AGA AGT ACG AGT
        Ser Ser Leu Asn Ile Thr His       Arg Thr  Arg  Arg Ser Thr Ser
                        *   468                                     478

Gly Asn Ala Thr His Leu Ser Asn Met Glu Ser Val His Asn
        GGC AAT GCA ACT CAT TTA TCC AAC ATG GAG TCG GTG CAC AAT
        GAC AAT ACA ACA CAT TTG TCC AGC ATG GAA TCG GTG CAC AAT
        Asp Asn Thr Thr His Leu Ser Ser Met Glu Ser Val His Asn
```

FIG. 2G

```
                   PstI                              488
      Leu Val Tyr Ala Gln Leu Gln Phe Thr Tyr Asp Thr Leu Arg Gly
1435  CTG GTC TAC GCC CAG CTG CAG TTC ACC TAT GAC ACG TTG CGC GGT
      CTG GTC TAC GCC CAG CTG CAG TTC ACC TAT GAC ACG TTG CGC GGT
      Leu Val Tyr Ala Gln Leu Gln Phe Thr Tyr Asp Thr Leu Arg Gly
                          498                                     508

Tyr Ile Asn Arg Arg Ala Leu Ala Gln Ile Ala Glu Ala Trp Cys Val
      TAC ATC AAC CGG CGG GCG CTG GCG CAA ATC GCA GAA GCC TGG TGT GTG
      TAC ATC AAC CGG CGG GCG CTG GCG CAA ATC GCA GAA GCC TGG TGT GTG
      Tyr Ile Asn Arg Arg Ala Leu Ala Gln Ile Ala Glu Ala Trp Cys Val
                                              *
                                             518

Asp Gln Arg Arg Thr Leu Glu Val Phe Lys Glu Leu Ser Lys Ile
1525  GAT CAA CGG CGC ACC CTA GAG GTC TTC AAG GAA CTT AGC AAG ATC
      GAT CAA CGG CGC ACC CTA GAG GTC TTC AAG GAA CTC AGC AAG ATC
      Asp Gln Arg Arg Thr Leu Glu Val Phe Lys Glu Leu Ser Lys Ile
                          528                                     538

Asn Pro Ser Ala Ile Leu Ser Ala Ile Tyr Asn Lys Pro Ile Ala
      AAC CCG TCA GCT ATT CTC TCG GCC ATC AAC AAA CCG ATT GCC
      AAC CCG TCA GCC ATT CTC TCG GCC ATT TAC AAC AAA CCG ATT GCC
      Asn Pro Ser Ala Ile Leu Ser Ala Ile Tyr Asn Lys Pro Ile Ala
                                             548

Ala Arg Phe Met Gly Asp Val Leu Gly Leu Ala Ser Cys Val Thr
1615  GCG CGT TTC ATG GGT GAT GTC CTG GGT CTG GCC AGC TGC GTG ACC
      GCG CGT TTC ATG GGT GAT GTC CTG GGC CTG GCC AGC TGC GTG ACC
      Ala Arg Phe Met Gly Asp Val Leu Gly Leu Ala Ser Cys Val Thr
                          558                                     568

Ile Asn Gln Thr Ser Val Lys Val Leu Arg Asp Met Asn Val Lys
      ATT AAC CAA ACC AGC GTC AAG GTG CTG CGT GAT ATG AAT GTG AAG
      ATC AAC CAA ACC AGC GTC AAG GTG CTG CGT GAT ATG AAC GTG AAG
      Ile Asn Gln Thr Ser Val Lys Val Leu Arg Asp Met Asn Val Lys
```

FIG. 2H

```
1705  Glu Ser Pro Gly Arg Cys Tyr Ser Arg Pro Val Val Ile Phe Asn
      GAA TCG CCA GGA CGC TGC TAC TCA CGA CCA GTG GTC ATC TTT AAT
      GAA TCG CCA GGA CGC TGC TAC TCA CGA CCC GTG GTC ATC TTT AAT
      Glu Ser Pro Gly Arg Cys Tyr Ser Arg Pro Val Val Ile Phe Asn
                          *                                     598
                         588

Phe Ala Asn Ser Ser Tyr Val Gln Tyr Gly Gln Leu Gly Glu Asp
      TTC GCC AAC AGC TCG TAC GTG CAG TAC GGT CAA CTG GGC GAG GAT
      TTC GCC AAC AGC TCG TAC GTG CAG TAC GGT CAA CTG GGC GAG GAC
      Phe Ala Asn Ser Ser Tyr Val Gln Tyr Gly Gln Leu Gly Glu Asp
                                                    608

Asn Glu Ile Leu Leu Gly Asn His Arg Thr Glu Cys Gln Leu
      AAC GAA ATC CTG TTG GGC AAC CAC CGC ACT GAG TGT CAG CTT
      AAC GAA ATC CTG TTG GGC AAC CAC CGC ACT GAG TGT CAG CTT
      Asn Glu Ile Leu Leu Gly Asn His Arg Thr Glu Cys Gln Leu
1795              BglII618                                    628

Pro Ser Leu Lys Ile Phe Ile Ala Gly Asn Ser Ala Tyr Glu Tyr
      CCC AGC CTC AAG ATC TTC ATC GCC GGC AAC TCG GCC TAC GAG TAC
      CCC AGC CTC AAG ATC TTC ATC GCC GGG AAC TCG GCC TAC GAG TAC
      Pro Ser Leu Lys Ile Phe Ile Ala Gly Asn Ser Ala Tyr Glu Tyr
                                                638

Val Asp Tyr Leu Phe Lys Arg Met Ile Asp Leu Ser Ser Ile Ser
      GTG GAC TAC CTC TTC AAA CGC ATG ATT GAC CTC AGC ATC TCC
      GTG GAC TAC CTC TTC AAA CGC ATG ATT GAC CTC AGC AGT ATC TCC
      Val Asp Tyr Leu Phe Lys Arg Met Ile Asp Leu Ser Ser Ile Ser
1885      SalI        648                                     658

Thr Val Asp Ser Met Ile Ala Leu Asp Ile Asp Pro Leu Glu Asn
      ACC GTC GAC AGC ATG ATC GCC CTA GAC ATC GAC CCG CTG GAA AAC
      ACC GTC GAC AGC ATG ATC GCC CTG GAT ATC GAC CCG CTG GAA AAT
      Thr Val Asp Ser Met Ile Ala Leu Asp Ile Asp Pro Leu Glu Asn
```

FIG. 21

```
                                                              Arg
       Thr Asp Phe Arg Val Leu Glu Leu Tyr Ser Gln Lys Glu Leu Arg
1975   ACC GAC TTC AGG GTA CTG GAA CTT TAC TCG CAG AAA GAA TTG CGT
       ACC GAC TTC AGG GTA CTG GAA CTT TAC TCG CAG AAA GAG CTG CGT
       Thr Asp Phe Arg Val Leu Glu Leu Tyr Ser Gln Lys Glu Leu Arg
                       678          XhoI                        688

Ser Ser Asn Val Phe Asp Leu Glu Glu Ile Met Arg Glu Phe Asn
       TCC AGC AAC GTT TTT GAT CTC GAG GAG ATC ATG CGC GAG TTC AAT
       TCC AGC AAC GTT TTT GAC CTC GAA GAG ATC ATG CGC GAA TTC AAC
       Ser Ser Asn Val Phe Asp Leu Glu Glu Ile Met Arg Glu Phe Asn
                                    698

Ser Tyr Lys Gln Arg Val Lys Tyr Val Glu Asp Lys Val Val Asp
2065   TCG TAT AAG CAG CGG GTA AAG TAC GTG GAG GAC AAG GTA GTC GAC
       TCG TAC AAG CAG CGG GTA AAG TAC GTG GAG GAC AAG GTA GTC GAC
       Ser Tyr Lys Gln Arg Val Lys Tyr Val Glu Asp Lys Val Val Asp
                                                                718

Pro Leu Pro Pro Tyr Leu Lys Gly Leu Asp Asp Leu Met Ser Gly
       CCG CTG CCG CCC TAC CTC AAG GGT CTG GAC GAC CTC ATG AGC GGC
       CCG CTA CCG CCC TAC CTC AAG GGT CTG GAC GAC CTC ATG AGC GGC
       Pro Leu Pro Pro Tyr Leu Lys Gly Leu Asp Asp Leu Met Ser Gly
               SacII                                  728

Leu Gly Ala Ala Gly Lys Ala Val Gly Val Val Ala Ile Gly Ala Val
2155   CTG GGC GCC GCG GGA AAG GCC GTT GGC GTA GCC ATT GGG GCC GTG
       CTG GGC GCC GCG GGA AAG GCC GTT GGC GTA GCC ATT GGG GCC GTG
       Leu Gly Ala Ala Gly Lys Ala Val Gly Val Val Ala Ile Gly Ala Val
                 738                                            748

Gly Gly Ala Val Ala Ser Val Val Glu Gly Val Ala Thr Phe Leu
       GGT GGC GCG GTG TCC GAA GGC GTT GCC ACC TTC CTC
       GGT GGC GCG GTG TCC GAA GGC GTT GCC ACC TTC CTC
       Gly Gly Ala Val Ala Ser Val Val Glu Gly Val Ala Thr Phe Leu
```

```
        Pro Tyr Thr Asn Glu Gln Ala Tyr Gln Met Leu Leu Ala Leu Val
2515    CCT TAC ACC AAC GAG CAG GCT TAC CAG ATG CTT CTG GCC CTG GTC
        CCT TAC ACC AAC GAG CAG GCT TAC CAG ATG CTT CTG GCC CTG GCC
        Pro Tyr Thr Asn Glu Gln Ala Tyr Gln Met Leu Leu Ala Leu Ala
                        858                                     868
                                                 *
        Arg Leu Asp Ala Gln Arg Ala Gln Gln Gln Asn Gly Thr Asp Ser
        CGT CTG GAC GCA GAG CGA GCG CAG CAG CAG AAC GGT ACA GAT TCT
        CGT CTG GAC GCA GAG CGA GCG CAG CAG CAG AAC GGT ACA GAT TCT
        Arg Leu Asp Ala Gln Arg Ala Gln Gln Gln Asn Gly Thr Asp Ser
                                                 878

Leu Asp Gly Gln Thr Gly Thr Gln Asp Lys Gly Gln Lys Pro Asn
2605    TTG GAC GGA CAG CAG ACT GGC ACG CAG GAC AAG GGA CAG AAG CCC AAC
        TTG GAC GGA CAG CAG ACT GGC ACG CAG GAC AAG GGA CAG AAG CCT AAC
        Leu Asp Gly Gln Thr Gly Thr Gln Asp Lys Gly Gln Lys Pro Asn
                                        888                     898

Leu Leu Asp Arg Leu Arg His Arg Lys Asn Gly Tyr Arg His Leu
        CTG CTA GAC CGA CTG CGA CAC CGA AAA AAC GGC TAC CGA CAC TTG
        CTG CTA GAC CGG CTG CGA CAT CGC AAA AAC GGC TAC AGA CAC TTG
        Leu Leu Asp Arg Leu Arg His Arg Lys Asn Gly Tyr Arg His Leu

Lys Asp Ser Asp Glu Glu Asn Val OP
2695    AAA GAC TCC GAC GAA GAG AAC GTC TGAACCAAGAGGAGAAAAAAAAA
        AAA GAC TCC GAC GAA GAG AAC GTC TGAACCAAGAGGAGAAAAAAAACT
        Lys Asp Ser Asp Glu Glu Asn Val OP
                                907

CTAGACAAAAAAAGTGACAGAGACTTGTGATATACGGGGTTAAACTGGACATCTAGGTGCT
AGACAAAAAATATTGACACAGAGACTTGTGATATACGGGGTTAAACTGGATATCTAGGTGC
```

FIG. 2L

```
2806  GCATGTGTATTGCTTTGTGATTTGCTTCGTAAGCTGTCAGCCTCTCACGGTCCGCTA
      TGCATGTGTATTTCTTTGTGATTTTGCTTCGTAAGCTGTCAGCCTCTCACGGTCCGCT

2926  TGTTTTCAACCCGTATCTGAGCGGCGCGTGACCGGCGGTGCGGTTGCGGTTGGCCGGCG
      ATGTTTTCAACCCGTATCTGAGCGGCGCGTGACCGGCGGTGACCGGCGGTGCGCGGTGGCCGGC
      TCAGCCGTTCGCAGCCCCGGCTCCGCGCAGGGCTCGGGCAAGCGGCCGCCACAGAAACAGT
      GTCAGCCGTTCGCAGCCCGGGCTCCGCGCAGGGCTCGGGCAAGCGGCCGCCACAGAAACAG

3046  TTTTGCAGATCGTGCCGCGAGGCGTCATGTTCGACGGTCAGACGGGGTTGATCAAGCATAA
      TTTTTGCAGATCGTGCCGCGAGGTGTCATGTTCGACGGTCAGACGGGGTTGATCAAGCATA

3046  GACGGGACGGTTGCCTCTCATGTTCTATCGAGAGATTAAACATTTGTTGAGTCATGACA
      AGACGGGACGGCTGCCTCTCATGTTCTATCGAGAGATTAAACATTTGTTGAGTCATGAC

3166  TGGTTTGGCCGTGTCCTTGGCGCCGAGACCCCTGGTGCGTGGTGGGACCTATTCGTTT
      ATGGTTTGGCCGTGTCCTTGGCGCCGAGACCCCTGGTGCGTGGGACCTATTCGTT

3166  TCACACCTACGATCAAACGGACGCCGTGCTCTTCTTCGACTCGCCGAAAACGTGCGC
      TTCACACCTACGATCAGACGGACGCCGTGCTCTTCTTCGACTCGCCGAAAACGTGTCG

3286  CGCGCTATCGTCAGCATCGGTGCCTTCGGGGAACGTGTTGCGTTTCTTCGGCCACAGA
      CCGCGCTATCGTCAGCATCGGTGCCTTCGGGGAACGTGTTGCGTTTCTTCGGGCCACAG

3286  ACACGGCTACAGTATCTGCGTC
      AACACGGCTACAGTATCTGCGT
```

FIG. 2M

Topographic Map of Neutralizing Domains on CMV gB

| 1 | 2a | 2b |
|---|----|----|
| 87-1 | 105-7 | 51-4 |
| 92-1 | 112-1 | 114-5 |
| 143-13 | 130-9 | |
| 177-3 | 244-4 | |
| 253-1 | 382-2 | |
| 358-5 | 395-1 | |
| 388-2 | 409-2 | |
| 424-1 | 434-1 | |
| 432-1 | 436-1 | |
| 442-1 | 446-1 | |

FIG. 4

METHOD TO DETECT CMV BY HYBRIDIZATION WITH A GP55 SPECIFIC DNA PROBE

This application is a divisional of U.S. application Ser. No. 08/341,293, filed Nov. 15, 1994 is now 5,547,834, which is a continuation of U.S. application Ser. No. 07/671, 790, filed Mar. 26, 1991, now abandoned claiming priority from International Application No. PCT/US89/00323 which designated the United States, which is a continuation-in-part of U.S. application Ser. No. 07/149,715 filed Jan. 29, 1988, now abandoned.

TECHNICAL FIELD

The invention relates to recombinant human cytomegalovirus (CMV) proteins, and is directed to the production of neutralizing forms of gB protein and truncated forms thereof, their vaccine potential, and diagnostic DNA fragments thereof.

BACKGROUND OF THE INVENTION

Human cytomegalovirus (CMV) is a ubiquitous agent in human populations. Infections are generally asymptomatic, but there can be serious medical manifestations of the disease in immunocompromised individuals (transplant recipients and AIDS patients) and in congenitally infected newborns. In immunodeficient patients, primary CMV infection and reactivation of latent virus is associated with serious disease including retinitis and pneumonia. CMV infection also predisposes the patient to fungal and bacterial infections. Congenital CMV infection of the fetus occurs in about 1% (36,000) of infants born in the U.S. per year. Of these infants 10–20% will have symptomatic infection at birth or within two years of birth with a mortality rate of 10–15%. Among the survivors, many will have mild to severe neurologic complications including hearing loss, learning disabilities and mental retardation.

Vaccines that prevent or reduce CMV-associated disease are clearly needed. The CMV (Towne) strain has been tested as a vaccine candidate in normal individuals and renal transplant patients (Quinnan, Jr., G. V. et al. (1984) *Am Intern Med* 101:478–483); (Plotkin, S. A. 1985, CMV Vaccines, In: The Herpes Viruses vol. 4, ed., Roizman and Lopez, Plenum Press, N.Y., p. 297–312). While this vaccine appeared to have no deleterious effects and did reduce symptoms of CMV disease in transplant recipients, there are many objections to the use of experimental live attenuated virus vaccines, including the possibility of immune impairment resulting from virus infection and reports of possible association between CMV and oncogenesis.

In the absence of a complete understanding of the biology of CMV, the most rational approach to a vaccine would involve the development of subunit vaccines based upon the surface glycoproteins of the virus using recombinant viral glycoproteins which elicit neutralizing antibodies.

Like other herpesviruses, CMV specifies multiple glycoproteins (Stinski, M. (1976) *J Virol* 19:594–609; Pereira, L., et al. (1982) *Infect Immun* 36:933–942). Characterization of these have involved studies of CMV-infected cells and purified virions using polyclonal and monoclonal antibodies (Pereira, L., et al. (1984) *Virology* 139:73–86; Britt, W. J. (1984) *Virology* 135:369–378; Nowak, B., et al. (1984) *Virology* 132:325–338; Law, K.M., et al. (1985) *J Med Virol* 17:255–266; Rasmussen, L., et al. (1984) *Proc Natl Acad Sci USA* 81:876–880; and Britt and Auger (1986) *J Virol* 58:185–191).

U.S. Pat. No. 4,689,225, issued Aug. 25, 1987 and based upon the work described in the Pereira et al. references, *supra*, describes a method and vaccine for CMV infections using a polypeptide designated therein as glycoprotein A (gA1–A7) of cytomegalovirus. Two glycoproteins designated p130 (gp130) and p55 (gp55) (based on the molecular weights given in kilodaltons) have been partially purified and shown to elicit a neutralizing response in guinea pigs (Rasmussen, L., et al. (1985) *J Virology* 55:274–280). The gp130 glycoprotein appears to be a precursor to the gp55 glycoprotein.

The gB gene from CMV strain AD169 (which appears to be similar to the p130 CMV protein described by Rasmussen et al., *supra*) has been identified by nucleotide sequencing (Cranage, M. P. et al. (1986) *EMBO J* 5(11):3057–3063) with a 906 amino acid protein deduced therefrom. The gB gene product was expressed in recombinant vaccinia virus and rabbits immunized with this gene product produced antibodies that immunoprecipitate gB from CMV-infected cells and neutralize CMV infectivity in vitro (See also WO 87/05326).

Although there is much ongoing activity towards both the identification of major gylcoproteins which are the targets for viral neutralization and the development of a subunit CMV vaccine, to date, the origin of the gp55 CMV glycoprotein has not been established nor has gp55 been identified by nucleotide or amino acid sequence and therefore, no vaccine composed of the 55,000 dalton recombinant viral gB protein or any truncated recombinant polypeptide thereof has been reported. Clearly, in light of the absence of a complete understanding of the biology of CMV, it would be desirable to provide a safe, effective and economic vaccine capable of affording protection against cytomegalovirus infections, as well as to provide diagnostic reagents capable of detecting the particular immunogenic stimulus resulting from CMV infections.

Disclosure of the Invention

The present invention provides recombinant polypeptides derived from the 55,000 dalton protein derived from gB and truncated fragments thereof which contain an epitope which is immunologically identifiable with one encoded by the CMV genome. A recombinant polypeptide derived from the gp55 CMV glycoprotein gB is provided in one embodiment of the invention.

The complete characterization of the gp55 protein derived from gB permits the production of polypeptides which are useful as standards or reagents in diagnostic tests and/or as components of vaccines. Since the desired polypeptide can be synthetically made in a relatively pure form or by recombinant DNA technology, the problems with other methods of immunogen and vaccine manufacture, including coproduction of competitive antigens and contaminants, are avoided.

In a preferred embodiment of the invention, the truncated gp55 gB fragment contains an epitope that is immunologically reactive with a CMV neutralizing antibody. The neutralizing antibody can be generated by techniques known in the art such as that described for monoclonal antibodies disclosed in Rasmussen et al., *supra* and U.S. Pat. No. 4,689,225.

Also provided in another preferred embodiment of the invention is a recombinant polypeptide encoded within CMV glycoprotein gB, which has a modified endoproteolytic cleavage site such that cleavage of the gB protein is effectively inhibited. The modification of the cleavage site is accomplished using site specific mutagenesis on the DNA encoding the polypeptide at or near the proteolytic cleavage site. Related to this aspect of the invention are the polynucleotides encoding the recombinant polypeptides.

Another aspect of the invention is a recombinant gp55 polynucleotide comprising a nucleotide sequence derived from the CMV gB gene. Related to this aspect of the invention are truncated recombinant polynucleotides containing regions encompassing nucleotides 1381 through 2040 of gp55 and nucleotides 1381 through 1938 of gp55, which regions contain an epitope which is immunologically reactive with a CMV neutralizing antibody.

Yet another aspect of the invention provides an expression system comprising host cells transformed with a vector containing the recombinant polynucleotides of the invention.

Another aspect of the invention provides a vaccine or prophylactic agent against human cytomegalovirus infection, said vaccine comprising a recombinant gp55 polypeptide derived from the CMV gB genome or the endoproteolytic cleavage site modified gB polypeptide in amounts effective to elicit viral neutralizing activity against cytomegalovirus when administered to a susceptible individual.

Still another aspect of the invention provides a vaccine against human cytomegalovirus infection, said vaccine comprising a recombinant polypeptide derived from a truncated fragment encoded within CMV glycoprotein gB wherein the truncated fragment contains an epitope which is immunologically reactive with a CMV neutralizing antibody, said recombinant polypeptide being present in an immunologically acceptable carrier in an amount effective to elicit viral neutralizing activity against cytomegalovirus when administered to a susceptible individual.

Another aspect of the invention provides for a DNA hybridization assay for detecting CMV homologous sequences in a biological sample comprising: a) incubating a biological sample with a DNA probe, which probe may be optionally labeled with an enzyme, radioactive tag or a fluorescent tag, under conditions which promote the formation of DNA duplexes, wherein said DNA probe is derived from gp55 nucleotide sequences; and b) detecting the formed DNA duplexes containing the DNA probe.

A further aspect of the invention provides an immunoassay for detecting antibodies directed against a CMV antigen in a biological specimen comprising:

(a) incubating a biological sample with a probe polypeptide under conditions which allow the formation of an antibody-antigen complex, wherein said probe polypeptide consists of the p55 CMV recombinant protein or a truncated fragment thereof and said protein or truncated fragment contains an epitope which is immunologically reactive with a CMV-neutralizing antibody; and (b) detecting an antibody-antigen complex containing the probe antigen.

Yet another aspect of the invention provides polyclonal antibodies against the recombinant gp55 or truncated polypeptides thereof, for immune prophylaxis.

Other and further aspects of the present invention will be apparent from the following description and claims and other embodiments of the invention employing the same or equivalent principles may be used by those skilled in the art without departing from the present invention and the purview of the appended claims.

Figure 1:
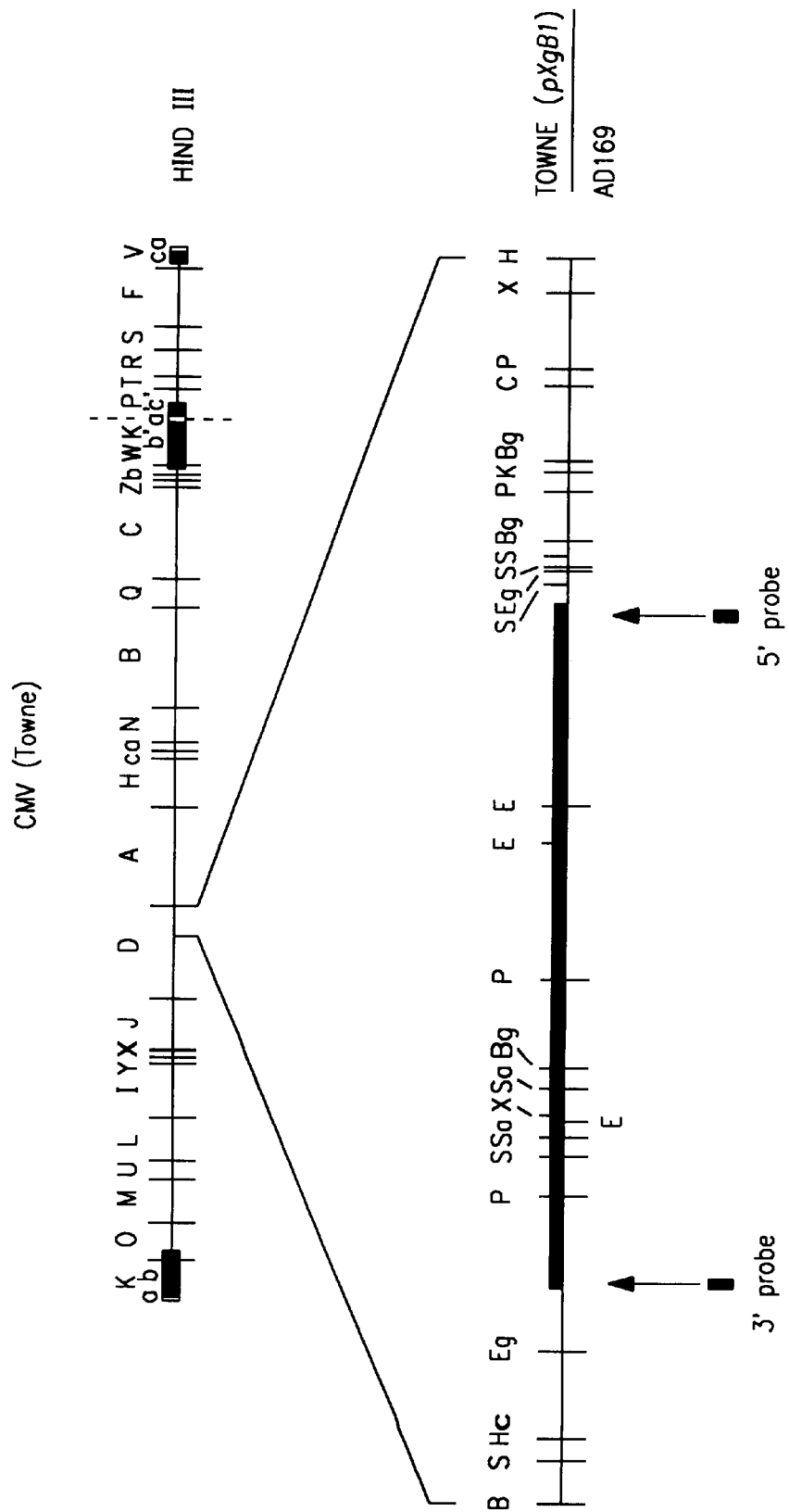
FIG. 1 is a HindIII restriction map of the CMV (Towne) genome displayed in the parental orientation. Unique sequences are denoted by a thin line, and inverted repeats of the Long (L), and Short (S) components are denoted by boxes, ab-b',a', and a'c'-ca. The a sequence, distinguished as a white box, is a terminal direct repeat with an inverted copy (a') at the L/S junction.
Figure 3A:
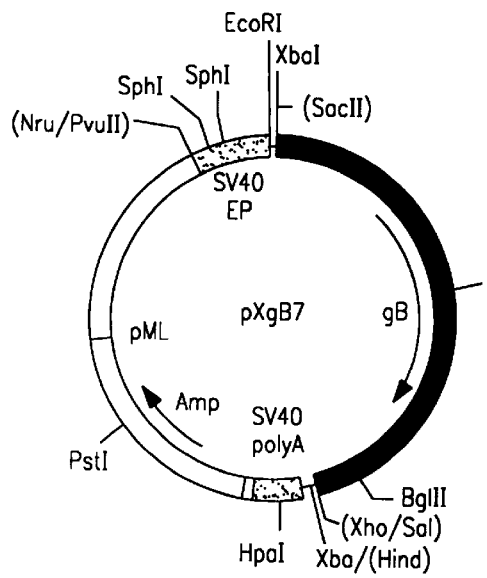
Figure 3B:
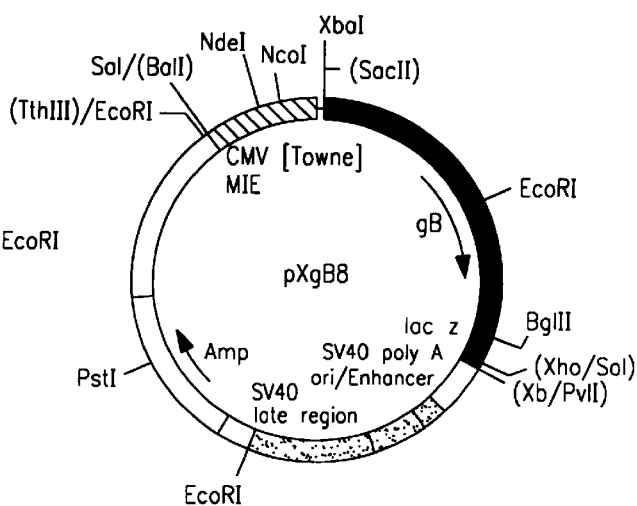
Figure 3C:
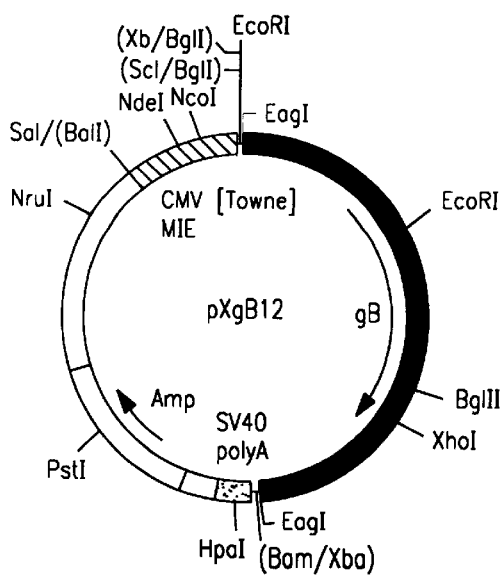
Figure 3D:
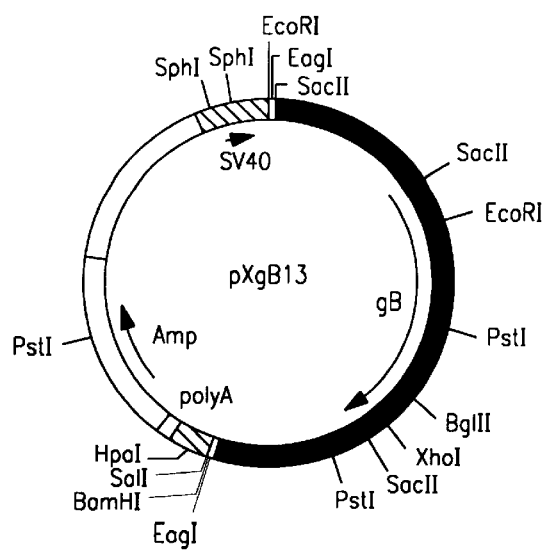

The lower restriction map illustrates the ~4.96 kb BamHI E/R to HindIII D/A fragment encoding the gB gene. The Towne DNA fragment cloned into pXgB1 is shown above the line and the largely colinear AD169 fragment is shown below the line. Restriction enzyme abbreviations are B, BamHI; Bg, BglII; C, ClaI; E, EcoRI; Eg, EagI; H, HindIII; Hc, HincII; K, KpnI; P, PstI; S, SacII; Sa, SalI; X, XhoI.

Figure 2C:
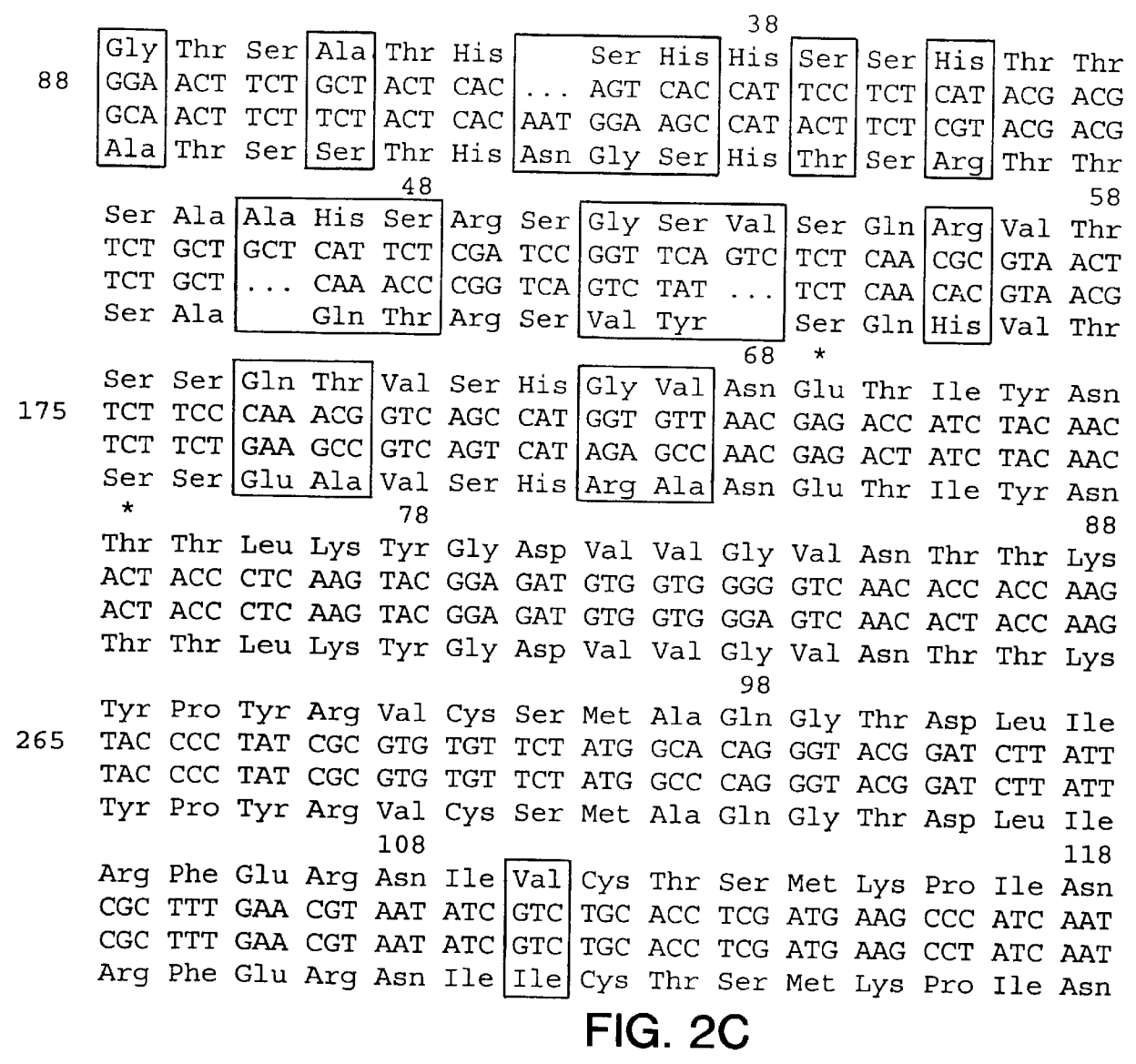
Figure 2K:
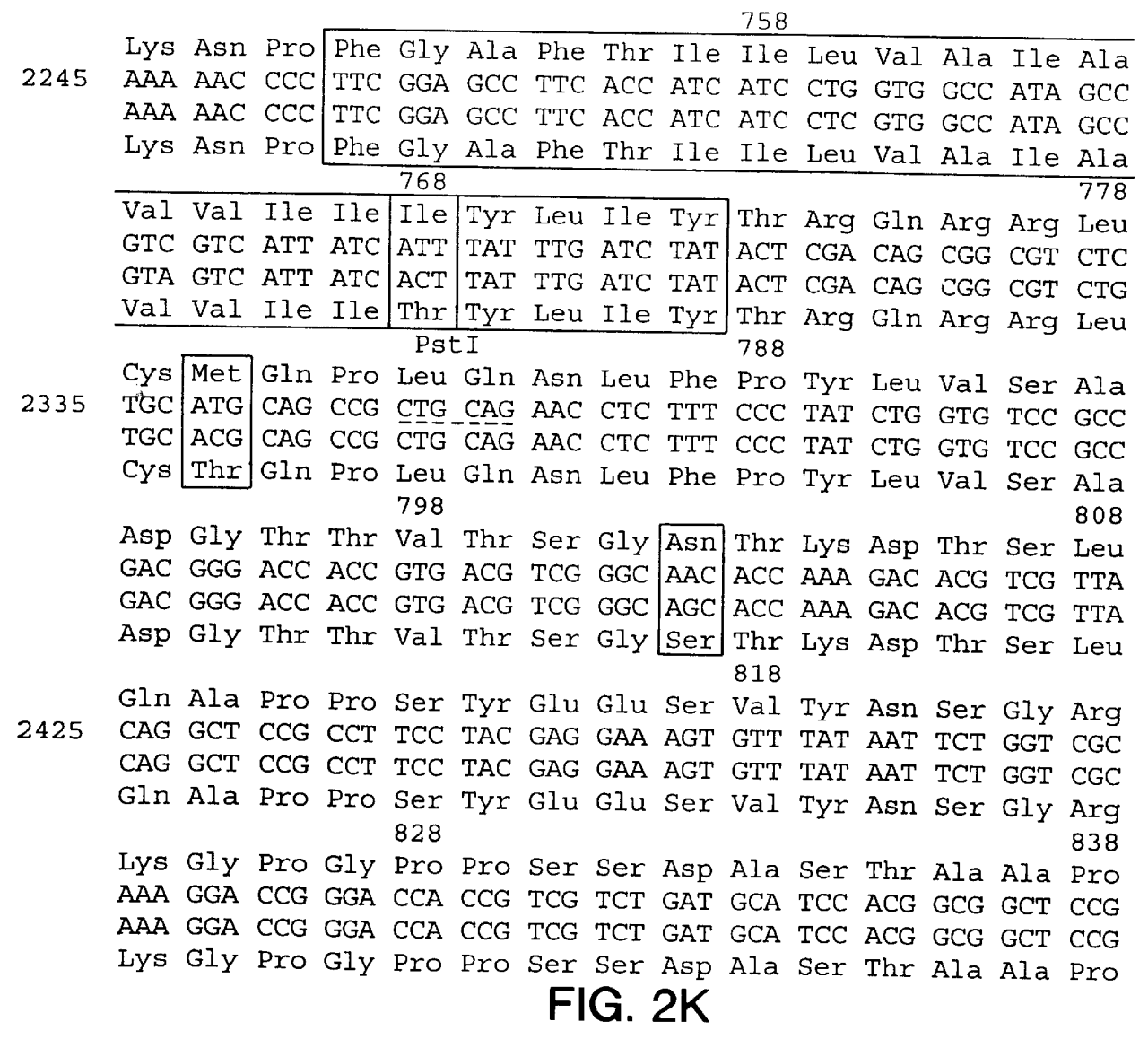

FIG. 2 illustrates the nucleotide and deduced amino acid sequences for the gB envelope protein of CMV strains Towne and AD169. The gp55 cleavage site between amino acids 460 and 461 is indicated by the arrow. The N-terminal sequence analysis of gp55, which revealed this cleavage site, is shown in Table 2.

FIG. 3 is an illustration of the mammalian cell expression vectors of the invention. Plasmids pXgB7 (4.5 kb) and pXgB8 (6.5 kb) encode a truncated version of gB cloned as a partial SacII/XhoI fragment into pSV7d, an SV40 based expression vector or pON260, a CMV-based expression vector, respectively. Plasmids pXgB12 (6.4 kb) and pXgB13 (5.5 kb) encode a full length gB gene cloned as an EagI fragment into plasmid PMIE, a CMV-based expression vector and pSV7d, respectively. Transcriptional initiation and termination elements differ among each construction.

FIG. 4 is a schematic representation of a topographical map of epitopes on CMV gB. Discontinuous neutralizing domains (domain 1=amino acids 461–619; domain 2$a$ and 2$b$=amino acids 620–680) are labeled by ellipses.

MODES FOR CARRYING OUT THE INVENTION

Definitions

As used herein, a polynucleotide "derived from" a designated sequence, for example, the DNA from the CMV gB gene, refers to a polynucleotide sequence which is comprised of a sequence of at least 6–20 nucleotides, more preferably at least 15 to 20 nucleotides corresponding, i.e., identical to or complementary to, a region of the designated nucleotide sequence. The correspondence to the nucleic acid sequence will be approximately 70% or greater, will preferably be at least 80%, and even more preferably will be at least 90%.

The correspondence or non-correspondence of the derived sequence to other sequence can be determined by hybridization under the appropriate stringency conditions, using standard DNA hybridization technologies in liquid phases or on solid supports. Hybridization techniques for determining the complementarity of nucleic acid sequences are known in the art (see, for example, Maniatis et al. (1982)), and are discussed *infra*. In addition, mismatches of duplex polynucleotides formed by hybridization can be determined by known techniques, including digestion with a nuclease such as S1 that specifically digests single-stranded areas in duplex polynucleotides. Regions from which typical DNA sequences may be "derived" include but are not limited to, regions encoding specific epitopes.

The derived polynucleotide is not necessarily physically derived from the nucleotide sequence shown, but may be generated in any manner, including for example, chemical synthesis or DNA replication or reverse transcription, which methods are based on the information provided by the sequence of bases in the region(s) from which the polynucleotide is derived.

Similarly, a polypeptide "derived from" a designated sequence, for example, the truncated CMV gB glycoprotein, refers to a polypeptide having an amino acid sequence identical to that of a polypeptide encoded in the sequence, or a protein thereof wherein the portion consists of at least 5–10 amino acids, and more preferably at least 10–15 amino acids, or which is immunologically identifiable with a polypeptide encoded in the sequence.

The term "recombinant polynucleotide" as used herein to characterize a polynucleotide useful for the production of CMV diagnostics and/or subunit vaccines intends a polynucleotide of genomic, cDNA, semisynthetic, or synthetic origin which, by virtue of its origin or manipulation: (1) is not associated with all or a portion of the polynucleotide with which it is associated in nature or in the form of a library; and/or (2) is linked to a polynucleotide other than that to which it is linked in nature.

"Recombinant host cells", "host cells", "cells", "cell lines", "cell cultures", and other such terms denoting prokaryotic microorganisms or eukaryotic cell lines cultured as unicellular entities, are used interchangeably, and refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered .by the above terms.

A "replicon" is any genetic element, e.g., a plasmid, a chromosome, a virus, that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Immunologically identifiable with/as" refers to the presence of epitope(s) in the non-native, i.e., artificially synthesized or recombinant protein, which are also present in and are unique to the designated CMV polypeptide(s). Immunological identity may be determined by antibody binding and/or competition in binding; these techniques are known to those of average skill in the art, and are also illustrated infra. The uniqueness of an epitope can also be determined by computer searches of known data banks, e.g. Genbank, for the polynucleotide sequences which encode the epitope, and by amino acid sequence comparisons with other known proteins.

As used herein, "epitope" refers to an antigenic determinant of a polypeptide; an epitope could comprise 3 amino acids in a spatial conformation which is unique to the epitope, generally an epitope consists of at least 5 such amino acids, and more usually, consists of at least 8–10 such amino acids.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an. antibody are known in the art.

The term "polypeptide" refers to the amino acid product of a sequence encoded within a genome, and does not refer to a specific length of the product, thus, peptides, oligopeptides, and proteins are included within the definition of polypeptide. This term also does not refer to post-expression modifications of the polypeptide, for example, glycosylations, acetylations, phosphorylations and the like.

"Transformation", as used herein, refers to the insertion of an exogenous polynucleotide into a host cell, irrespective of the method used for the insertion, for example, direct uptake, transduction, or f-mating. The exogenous polynucleotide may be maintained as a non-integrated vector, for example, a plasmid, or alternatively, may be integrated into the host genome.

"Treatment" as used herein refers to prophylaxis and/or therapy.

An "individual", as used herein, refers to vertebrates, particularly members of the mammalian species, and includes but is not limited to domestic animals, sports animals, primates, and humans.

The DNA encoding the desired polypeptide, whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell lines is given in Section III.A., infra. The polypeptide is then isolated from lysed cells or from the culture medium and purified to the extent needed for its intended use. Purification may be by techniques known in the art, for example, salt fractionation, chromatography on ion exchange resins, affinity chromatography, centrifugation, and the like. See, for example, Methods in Enzymology for a variety of methods for purifying proteins. Such polypeptides can be used as diagnostics, or those which give rise to neutralizing antibodies may be formulated into vaccines. Antibodies raised against these polypeptides can also be used as diagnostics, or for passive immunotherapy.

DESCRIPTION OF THE INVENTION

The glycoprotein which is the subject of the present invention, the 55,000 dalton glycoprotein encoded by the glycoprotein B gene, has been shown to induce neutralizing antibodies against CMV (Rasmussen, et al. 1985, *supra*). In particular, the polypeptides of the present invention correspond to proteins of the viral genome which are homologous to certain portions of the CMV gB envelope protein gp130 and the gp55 derived thereof.

Referring now to FIG. 2 showing the nucleotide and deduced amino acid sequences for the gB envelope protein of CMV strains Towne and AD169, the gp55 recombinant protein of the present invention is a 447 amino acid protein beginning at its amino terminus with serine at residue 461 ($Ser_{461}$) and terminating at valine residue 907 ($Val_{907}$). Truncated forms of this protein of particular interest contain substantial amino acid sequence homology to the region of gp55 which contains epitopes that are immunologically reactive with CMV neutralizing antibodies. Generally, this region of the CMV envelope protein lies within residue 461 to about residue 680. More particularly, discontinuous neutralizing domains have been localized: domain 1 spans amino acids 461–619 and domains 2a and 2b span amino acids 620–680.

In order to determine the region of gB containing these neutralizing epitopes, the nucleotide sequence of the Towne gB gene was first determined. The Towne strain was chosen because of its demonstrated safety as a vaccine. A restriction map of the analogous HindIII D fragment of CMV (Towne) was derived. A 4.96 kb HindIII to BamHI fragment from the right end of HindIII D, which was likely to encode gB (see FIG. 1), was subcloned. In FIG. 1, the restriction map for the Towne strain is compared to the same region of the AD169 strain. The nucleotide sequence of the gB region was determined from the 5' most distal PstI site to the HincII site 3' to the gB coding sequence (FIG. 1). In FIG. 2, the gB (Towne) sequence is shown on the top line and, for comparison, the DNA sequence of the CMV (AD169) gB region is shown on the bottom line.

The Towne gB gene is encoded by an open reading frame of 2721 basepairs. Two other long open reading frames (ORF) are also present in the Towne sequence shown in FIG. 2. The second ORF, which is out of frame with respect to the gB gene, extends from the HindIII D/A site (not shown) through the 5' untranslated region of the gB gene and terminates at nucleotide +36. The third ORF, also out of frame with respect to the gB gene, starts at nucleotide +2864 and extends through to the end of the sequence shown in FIG. 2.

The size of the gB protein predicted from the 2721 bp ORF is 907 amino acids long and has features characteristic of a membrane protein. A potential 24 amino acid signal sequence is shown in FIG. 2 ($Met_1$ to $Ser_{24}$). The signal domain contains a hydrophobic core ($Ile_5$ to $Val_{23}$, with the exception of $Asn_{13}$) preceded by a charged residue ($Arg_4$).

Full length and truncated versions of the gB gene were cloned into plasmids suitable for expression in mammalian cells. The construction of these plasmids is described in detail in the examples which follow. Truncated forms of the gB gene were constructed by deleting amino acids 681 to 907 and 647 to 907 at the C-terminus, removing the transmembrane and C-terminal domains.

The expression of the gB gene encoded by the full length and truncated constructs was analyzed by transient expression in COS-7 cells using the virus neutralizing murine monoclonal antibody 15DB (described by Rasmussen et al., 1985, *supra*) as a probe for expression. This antibody is directed against a 55 kd virion glycoprotein (gp55) and a related 130 kd (gp130) intracellular precursor. The antibody 15DB can neutralize a wide range of clinical and laboratory strains in the presence of complement thereby establishing this gB epitope as an important target for virus neutralizing antibody.

The expression of truncated forms of the gB protein was also analyzed using panels of monoclonal antibodies described in U.S. Pat. No. 4,689,225. Of these antibodies, ten with complement-dependent and independent neutralizing activity reacted with a truncated derivative of gB (gBt) that contained 619 amino terminal residues but lacks the transmembrane and intracellular region of the molecule. Twelve antibodies reacted with a CHO cell line expressing a 680 amino C-terminal deleted gB derivative (CHO cell line 67).

In addition, a gB polypeptide having a mutagenized endoproteolytic cleavage site is provided herein. Results obtained using a calcium-specific ionophore A23187 to inhibit cleavage of the gB molecule expressed in a stable CHO cell line (67.77), indicate the feasibility of expressing a 110 kilodalton uncleaved gB protein, i.e., which lacks the transmembrane and putative cytoplasmic domains. The ability to express the gB molecule without subsequent processing permits the production of the desired protein free from other contaminating or undesirable gB products.

Mutagenesis oligonucleotides, designed to change the amino acid sequence at or near the proteolytic cleavage site in a conservative manner, are used to substitute, for example, threonine or glutamine residues for arginine or lysine, at positions −1, −2 and −4 relative to the point of cleavage after amino acid $Arg_{460}$.

These endoproteolytic cleavage site mutants, upon expression in mammalian cell expression vectors, are tested for resistance to proteolysis and radiolabeled cell lysates and conditioned medias of cells receiving these constructs are radioimmunoprecipitated with neutralizing monoclonal antibodies to analyze gB expression.

Preparation of Antigenic Polypeptides and Conjugation with Carrier

An antigenic region of a polypeptide is generally relatively small - - - typically 8 to 10 amino acids or less in length. Fragments of as few as 5 amino acids may characterize an antigenic region. DNAs encoding short segments of CMV gB polypeptides can be expressed recombinantly either as fusion proteins, or as isolated polypeptides. In addition, short amino acid sequences can be conveniently obtained by chemical synthesis. In instances wherein the synthesized polypeptide is correctly configured so as to provide the correct epitope, but is too small to be immunogenic, the polypeptide may be linked to a suitable carrier.

A number of techniques for obtaining such linkage are known in the art, including the formation of disulfide linkages using N-succinimidyl-3-(2-pyridyl-thio)propionate (SPDP) and succinimidyl 4-(N-maleimido-methyl) cyclohexane-l-carboxylate (SMCC) obtained from Pierce Company, Rockford, Ill. (If the peptide lacks a sulfhydryl group, this can be provided by addition of a cysteine residue.) These reagents create a disulfide linkage between themselves and peptide cysteine residues on one protein and an amide linkage through the epsilon-amino on a lysine, or other free amino group in the other. A variety of such disulfide/amide-forming agents are known. See, for example, *Immun Rev* (1982) 62:185. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2-nitro-4-sulfonic acid, sodium salt. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, tetanus toxoid, and other proteins well known to those skilled in the art.

Preparation of Hybrid Particle Immunogens Containing CMV Epitopes

The immunogenicity of the epitopes of CMV may also be enhanced by preparing them in mammalian or yeast systems fused with particle-forming proteins such as that associated with hepatitis B surface antigen. Constructs wherein the CMV epitope is linked directly to the particle-forming protein coding sequences produce hybrids which are immunogenic with respect to the CMV epitope. In addition, all of the vectors prepared include epitopes specific to HBV, having various degrees of immunogenicity, such as, for example, the pre-S peptide. Thus, particles constructed from particle forming protein which include CMV sequences are immunogenic with respect to CMV and HBV.

Hepatitis surface antigen (HBSAg) has been shown to be formed and assembled into particles in *S. cerevisiae* (Valenzuela, et al. (1982) *Nature* 298:344), as well as in, for example, mammalian cells (Valenzuela, P., et al. (1984), in Hepatitis B (Millman, I., ed., Plenum Press) pp. 225–236). The formation of such particles has been shown to enhance the immunogenicity of the monomer subunit. The constructs may also include the immunodominant epitope of HBSAg, comprising the 55 amino acids of the presurface (pre-S) region. Neurath, et al. (1984). Constructs of the pre-S-HBSAg particle expressible in yeast are disclosed in European Patent Publication 174,444; hybrids including heterologous viral sequences for yeast expression are disclosed in European Patent Publication 175,261. Both applications are assigned to the herein assignee, and are incorporated herein by reference. These constructs may also be expressed in mammalian cells such as Chinese hamster ovary (CHO) cells using an SV40-dihydrofolate reductase vector (Michelle, et al. (1984) *Int Symposium on Viral Hepatitis*).

Preparation of Vaccines

Vaccines may be prepared from one or more immunogenic polypeptides encoded within the recombinant polynucleotide sequences of gB.

In addition, prophylactic agents comprising the 110 kilodalton uncleaved C-terminal truncated gB protein, are also useful to assess the effects of processing on CMV infectivity and pathogenicity. As demonstrated for several other viruses (hemagglutinin of influenza virus and HIV gp160), endoproteolytic cleavage of precursor polypeptides is an essential step in the maturation of viral peptides, that is, for viral replication and infectivity. The present endoproteolytic cleavage site mutants, in addition to eliminating the production of multiple processed forms of gB, are believed to permit the generation of a viral neutralizing response in a subject without concomitant risk of introducing an active infection.

The preparation of vaccines which contain immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween 80 emulsion. The effectiveness of an adjuvant may be determined by measuring the amount of antibodies directed against an immunogenic polypeptide containing a CMV antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkaline glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Dosage and Administration of Vaccines

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or re-enforce the immune response, for example, at 1–4 months for a second dose, and if needed, a subsequent dose(s) after several months.

Preparation of Antibodies Against CMV Epitopes

The immunogenic polypeptides prepared as described above may be used to produce antibodies, both polyclonal and monoclonal. If polyclonal antibodies are desired, a selected mammal (e.g., mouse, rabbit, goat, guinea pig, horse, etc.) is immunized with an immunogenic polypeptide bearing a CMV epitope(s). Serum from the immunized animal is collected and treated according to known procedures. If serum containing polyclonal antibodies to a CMV epitope contains antibodies to other antigens, the polyclonal antibodies can be purified by immunoaffinity chromatography. Techniques for producing and processing polyclonal antisera are known in the art, see for example, Mayer and Walker, eds., (1987) *Immunochemical Methods in Cell and Molecular Biology,* Academic Press, London.

Monoclonal antibodies directed against CMV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Rasmussen et al. (1985) *supra;* M. Schreier, et al. (1980) Hybridoma Techniques; Hammerling, et al. (1981) Monoclonal Antibodies and T-Cell Hybridomas; Kennett, et al. (1980) Monoclonal Antibodies; see also, U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against CMV epitopes can be screened for various properties; i.e., for isotype, epitope affinity, etc.

Antibodies, both monoclonal and polyclonal, which are directed against CMV epitopes are particularly useful in diagnosis, and those which are neutralizing are useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. Techniques for raising anti-idiotype antibodies are known in the art. See, for example, Grzych et al. (1985) *Nature* 316:74 and Macnamara et al. (1984) *Science* 226:1325. Generally, the truncated CMV recombinant peptides described herein containing CMV neutralizing epitopes would be used to generate monoclonal antibodies from which anti-idiotype antibodies could be generated. These anti-idiotype antibodies may also be useful for treatment of CMV, as well as for an elucidation of the immunogenic regions of CMV antigens.

Diagnostic Oligonucleotide Probes and Kits

Using the disclosed CMV DNA as a basis, oligomers of approximately 8 nucleotides or more can be prepared, either by excision or synthetically, which hybridize with the CMV gB gene and are useful in the detection of unique viral sequences by hybridization. While 6–8 nucleotides may be a workable length, sequences of 10–12 nucleotides are preferred, and about 20 nucleotides appears optimal. Preferably, these sequences will derive from regions which lack heterogeneity. These probes can be prepared using routine methods, including automated oligonucleotide synthetic methods. For use as probes, complete complementarity is desirable, though it may be unnecessary as the length of the fragment is increased.

For use of such probes as diagnostics, the biological sample to be analyzed, such as blood or serum, is treated, if desired, to extract the nucleic acids contained therein. The resulting nucleic acid from the sample may be subjected to gel electrophoresis or other size separation techniques; alternatively, the nucleic acid sample may be dot blotted without size separation. The probes are then labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the CMV gB gene. Therefore, usually high stringency conditions are desirable in order to prevent false positives. However, conditions of high stringency should only be used if the probes are complementary to regions of the viral gene which lacks heterogeneity. The stringency of hybridization is determined by a number of factors during hybridization and during the washing procedure, including temperature, ionic strength, length of time, and concentration of formamide. These factors are outlined in, for example, Maniatis, T. (1982).

Generally, it is expected that the CMV genome sequences will be present in serum of infected individuals at relatively low levels, i.e., at approximately $10^2$–$10^3$ sequences per ml. This level may require that amplification techniques be used in hybridization assays. Such techniques are known in the art. For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT application 84/03520 and EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands. A particularly desirable technique may first involve amplification of the target CMV sequences in sera approximately 10,000 fold, i.e., to approximately $10^6$ sequences/ml. This may be accomplished, for example, by the technique of Saiki et al. (1986) *Nature* 324:163. The amplified sequence(s) may then be detected using a hybridization assay which is described in copending U.S. application Ser. No. 109,282, which was filed Oct. 15, 1987, is assigned to the herein assignee, and is hereby incorporated herein by reference. This hybridization assay, which should detect sequences at the level of $10^6$/ml utilizes nucleic acid multimers which bind to single-stranded analyte nucleic acid, and which also bind to a multiplicity of single-stranded labeled oligonucleotides. A suitable solution phase sandwich assay which may be used with labeled polynucleotide probes, and the methods for the preparation of probes is described in copending European Patent Publication No. 225,807, published Jun. 16, 1987, which is assigned to the herein assignee, and which is hereby incorporated herein by reference.

Immunoassay and Diagnostic Kits

Both the recombinant polypeptides which react immunologically with serum containing CMV antibodies, and the antibodies raised against these recombinant polypeptides, are useful in immunoassays to detect the presence of CMV antibodies, or the presence of the virus, in biological samples, including for example, blood or serum samples. Design of the immunoassays is subject to a great deal of variation, and a variety of these are known in the art. For example, the immunoassay may utilize one viral antigen, for example a recombinant polypeptide derived from amino acids 461–680 of gp55; alternatively, the immunoassay may use a combination of viral antigens derived from the CMV genome. It may use, for example, a monoclonal antibody directed towards one viral antigen, a combination of monoclonal antibodies directed towards the one viral antigen, monoclonal antibodies directed towards different viral antigens, polyclonal antibodies directed towards the same viral antigen, or polyclonal antibodies directed towards different viral antigens. Protocols may be based, for example, upon competition, or direct reaction, or may be sandwich type 1. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the recombinant polypeptides of the invention containing CMV epitopes or antibodies directed against epitopes in suitable containers, along with the remaining reagents and materials required for the conduct of the assay, as well as a suitable set of assay instructions.

The polynucleotide probes can also be packaged into diagnostic kits. Diagnostic kits include the probe DNA, which may be labeled; alternatively, the probe DNA may be unlabeled and the ingredients for labeling may be included in the kit. The kit may also contain other suitably packaged reagents and materials needed for the particular hybridization protocol, for example, standards, as well as instructions for conducting the test.

General Methods

The general techniques used in extracting the genome from a virus, preparing and probing a cDNA library, sequencing clones, constructing expression vectors, transforming cells, and the like are known in the art and laboratory manuals are available describing these techniques. However, as a general guide, the following sets forth some sources currently available for such procedures, and for materials useful in carrying them out.

Hosts and Expression Control Sequences

Both prokaryotic and eukaryotic host cells may be used for expression of desired coding sequences when appropriate control sequences which are compatible with the designated host are used. Among prokaryotic hosts, E. coli is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang, et al. (1977) Nature 198:1056), the tryptophan (trp) promoter system (Goeddel, et al. (1980) Nuc Acids Res 8:4057) and the lambda-derived $P_L$ promoter (Shimatake, et al. (1981) Nature 292:128) and N gene ribosome binding site and the hybrid tac promoter (De Boer, et al. (1983) Proc Natl Acad Sci USA 69:2110) derived from sequences of the trp and lac Uv5 promoters. The foregoing systems are particularly compatible with E. coli; if desired, other prokaryotic hosts such as strains of Bacillus or Pseudomonas may be used, with corresponding control sequences.

Eukaryotic hosts include yeast and mammalian cells in culture systems. Saccharomyces cerevisiae and Saccharomyces carlsbergensis are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach, et al. (1983) Meth Enz 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess, et al. (1968) J Acv Enz Req 7:149; Holland, et al. (1978) Biotechnology 17:4900), including the promoter for 3 phosphoglycerate kinase (Hitzeman (1980) J Biochem 255:2073). Terminators may also be included, such as those derived from the enolase gene (Holland (1981) J Biol Chem 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor. In addition, the transcriptional regulatory region and the transcriptional initiation region which are operably linked may be such that they are not naturally associated in the wild-type organism. These systems are described in detail in U.S. Ser. Nos. 468,589, 522,909, 760,197, and 868,639, filed Feb. 22, 1983, Aug. 12, 1983, Jul. 29, 1985, and May 29, 1986 respectively, all of which are assigned to the herein assignee, and are hereby incorporated herein by reference.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines including myeloma lines. Suitable promoters for mammalian cells are also known in the art and include viral promoters such as that from Simian Virus 40 (SV40) (Fiers (1978)), Rous sarcoma virus (RSV), adenovirus (ADV), human, simian, and murine CMV, and bovine papilloma virus (BPV). Mammalian cells may also require terminator sequences. Vectors suitable for replication in mammalian cells may include viral replicons, or sequences which insure integration of the appropriate sequences encoding CMV epitopes into the host genome.

Expression may also be carried out with 1 vectors, for example, baculovirus vectors, in transformed, cultured insect cells. Methods for insect cell cultures using, for example, Spodoptera frugiperda, are well known in the art and detailed procedures for their cultivation and use can be found in *A Manual of Methods for Baculovirus Vectors and Insect Cell Culture Procedures* by M. D. Summers and G. E. Smith, Texas Agricultural Experimental Station Bulletin No. 1555, 2nd printing Feb. 1988, and in EPA 127,839 published Dec. 12, 1984, to Smith, G. E. et al.

Transformations

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. For example, transformation of the E. coli host cells with lambda-gt11 containing CMV sequences is discussed in the Example section, *infra*. Bacterial transformation by direct uptake generally employs treatment with calcium or rubidium chloride (Cohen (1972) *Proc Natl Acad Sci USA* 69:2110; Maniatis et al. (1982) *Molecular Cloninq; A Laboratory Manual*, Cold Spring Harbor Press, Cold Spring Harbor, N.Y.). Yeast transformation by direct uptake may be carried out using the method of Hinnen, et al. (1978) *Proc Natl Acad Sci USA* 75:1929. Mammalian transformations by direct uptake may be conducted using the calcium phosphate precipitation method of Graham and van der Eb (1978) *Virology* 52:546, or the various known modifications thereof.

Vector Construction

Vector construction employs techniques which are known in the art. Site-specific DNA cleavage is performed by treating with suitable restriction enzymes under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures found in Methods in Enzymology (1980) 65:499–560.

Sticky ended cleavage fragments may be blunt ended using E. coli DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as E. coli, and successful transformants selected by, for example, antibiotic resistance, and screened for the correct construction.

Construction of Desired DNA Sequences

Synthetic oligonucleotides may be prepared using an automated oligonucleotide synthesizer as described by Warner (1984). If desired the synthetic strands may be labeled with $^{32}$P by treatment with polynucleotide kinase in the presence of $^{32}$P-ATP, using standard conditions for the reaction.

DNA sequences, including those isolated from cDNA libraries, may be modified by known techniques, including, for example site directed mutagenesis, as described by Zoller (1982) *Nuc Acids Res* 10:6487. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

Hybridization with Probe

DNA libraries may be probed using the procedure of Grunstein and Hogness (1975) *Proc Natl Acad Sci USA* 73:3961. Briefly, in this procedure, the DNA to be probed is immobilized on nitrocellulose filters, denatured, and prehybridized with a buffer containing 0–50% formamide, 0.75 M NaCl, 75 mM Na citrate, 0.02% (wt/v) each of bovine serum albumin, polyvinyl pyrollidine, and Ficoll, 50 mM Na Phosphate (pH 6.5), 0.1% SDS, and 100 micrograms/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40–42° C., and a high percentage, e.g., 50%, formamide. Following prehybridization, 5'-$^{32}$P-labeled oligonucleotide probe is added to the buffer, and the filters are incubated in this mixture under hybridization conditions. After washing, the treated filters are subjected to autoradiography to responding locations on the original agar plates is used as the source of the desired DNA.

Verification of Construction and Sequencing

For routine vector constructions, ligation mixtures are transformed into E. coli strain HB101 or other suitable host, and successful transformants selected by antibiotic resistance or other markers. Plasmids from the transformants are then prepared according to the method of Clewell, et al. (1969) *Proc Natl Acad Sci USA* 62:1159, usually following chloramphenicol amplification (Clewell (1972) *J Bacteriol* 110:667). The DNA is isolated and analyzed, usually by restriction enzyme analysis and/or sequencing. Sequencing may be by the dideoxy method of Sanger, et al. (1977) *Proc Natl Acad Sci USA* 74:5463 as further described by Messing, et al. (1981) *Nuc Acids Res* 9:309, or by the method of Maxam, et al. (1980) *Meth Enz* 65:499. Problems with band compression, which are sometimes observed in GC rich regions, were overcome by use of T-deezaguanosine according to Barr, et al. (1986) *Biotechniques* 4:428.

Purification of gB Produced by CHO Cell Lines

A number of conventional protein purification techniques are available for use in the purification of gB. These procedures include, for example, chromatographic methods such as ion exchange, hydrophobic interaction, lentil lectin chromatography and gel permeation chromatography.

EXAMPLES

Described below are examples of the present invention which are provided only for illustrative purposes, and not to limit the scope of the present invention.

Cells, Virus and Plasmids. Human CMV (Towne) was obtained from E. S. Mocarski (Stanford University). Virus was grown in cultures of human foreskin fibroblast (HF) cells with Dulbecco's modified Eagle medium (DME) (Gibco Laboratories, Grand Island, N.Y.) according to the procedure of Spaete and Mocarski (1985a) *J Virol* 56:135–143, but supplemented with 10% fetal calf serum (FCS) (Hyclone, Logan, UT).

Plasmid Constructions. The HindIII D fragment of CMV (Towne), illustrated in FIG. 1, was cloned into plasmid pBR322 and designated pRL104a, which was a gift of R. L. La Femina and G. S. Hayward (Johns Hopkins University). Plasmid pXgB1, which encodes the entire gB gene, was derived from circularization of the 8.95 kb BamHI fragment of pRL104a. Thus, pXgB1 contains a 4.96 kb HindIII D/A to BamHI E/R fragment from the right end of HindIII D plus pBR322 sequences. Plasmid pXgB7 contains a truncated gB gene cloned into the expression vector pSV7d (Truett, M.A., et al. (1985) *DNA* 4:333–349) which contains the SV40 early promoter, origin and polyadenylation sequences, as well as sequences derived from pML. Plasmid pXgB7 was constructed by cloning gB as a 2.12 kb partial SacII/XhoI fragment into the SalI site of the pGEM-1 (Promega Biotec, Madison, Wis.) polylinker using the Klenow fragment (Boehringer Mannheim Biochemicals) to blunt the SacII site and to fill the unligated SalI site. This intermediate construct was designated pXgB6. The gB sequence was excised from the surrounding polylinker sequences of pXgB6 as a 2.13 kb XbaI/HindIII fragment and inserted into the XbaI site of pSV7d. The HindIII site was filled and ligated to the filled XbaI site of pSV7d to preserve the XbaI site at the 3'-end of gB. The resulting plasmid was designated pXgB7 and is shown in FIG. 3.

Plasmid pXgB8 contains the same truncated gB sequences cloned into pON260, a CMV major immediate early (MIE) promoter driven beta-galactosidase (lacZ) expression vector. Plasmid pON260 is derived from pON249 (Geballe, A.P., et al. (1986) *Cell* 46:865–872) by removal of a BalI to SalI fragment upstream from the CMV enhancer. The 2.13 kb XbaI fragment encoding gB was excised from pxgB7 and transferred to pON260, which had been cut with XbaI and PvuII to remove all but 15 C-terminal amino acids of the lacZ coding sequences. These lacZ sequences are not expressed in pXgB8 due to the presence of an upstream stop codon. Another CMV MIE promoter based expression plasmid, pMIE was constructed to eliminate the lacZ coding sequences resident in pON260. CMV MIE promoter sequences from the first BalI site upstream of the enhancer to the SacI site 8 bp downstream of the TATA box were removed from pON260 as a 0.67 kb SalI/XbaI fragment and cloned into plasmid pSV7b, a construct resembling pSV7d, which had been digested with SalI and BglII to remove the SV40 enhancer, origin and promoter leaving the SV40 polyadenylation signals intact.

The full length gB gene was cloned into pMT11/EagI (a pBR322-derived plasmid vector described by Spaete et al., 1985a) as a 3.12 kb EagI fragment in both orientations and the plasmids were designated pXgB9 and pXgB11. The gB sequences were excised from plasmid pXgB11 using the EcoRI and BamHI sites in the polylinker and cloned into PMIE polylinker sequences at EcoRI and XbaI. The resulting plasmid was designated pXgB12 and is illustrated in FIG. 3.

The EcoRI/BamHI fragment used to generate pXgB12 was also cloned into the polylinker sequences of pSv7d cut with EcoRI and BamHI. This SV40 expression plasmid was designated pXgB13 and is also illustrated in FIG. 3.

The gB gene cloned in pXgB6 was deleted by removing 1106 bp of N-terminal gB coding sequences between the AatII site and the NdeI site. The ends were blunted using the Klenow fragment and religated to create a SnaBI site and preserve the reading frame. This plasmid was designated pXgB19. A 1036 bp XbaI/HindIII fragment encoding the deleted gB gene was excised from pXgB19 and cloned into the unique SalI site of pMCMVAdhfr using Klenow to fill the sites prior to ligation of the blunt ends. The expression vector, pMCMVAdhfr, is colinear with pCMVAdhfr, described below, except that the human CMV promoter has been substituted by the murine CMV (MCMV) immediate early promoter cloned as a HpaI/PstI fragment.

To develop plasmids expressing uncleaved gB, the endoproteolytic cleavage site of gB is mutagenized in vitro using M13 cloned templates and the four mutagenesis oligonucleotides described below:

```
                         +1  *-1 -2  -3  -4
                         Ser Arg Lys Thr Arg
         Parent 5' GCC ATC TGT ACT TCT TTT GGT TCT ATT ATG AGT AAG Thr
         1.     5' GCC ATC TGT ACT TGT TTT GGT TCT ATT ATG AGT AAG Gln
         2.     5' GCC ATC TGT ACT TCT TTG GGT TCT ATT ATG AGT AAG Thr
         3.     5' GCC ATC TGT ACT TCT TTT GGT TGT ATT ATG AGT AAG Thr Gln     Thr
         4.     5' GCC ATC TGT ACT TGT TTG GGT TGT ATT ATG AGT AAG
```

A search of the gB and M13 sequences has revealed no potential binding sites for these 36 mers other than the cleavage site. A sequencing primer, 5' CGC CCG GTT GAT GTA ACC GCG 3', which lies 93 bp from the cleavage site, is also generated. The template strand is primed with each of the mutagenesis oligonucleotides followed by elongation. The resulting dsDNA is used to transform a suitable M13 host strain and the mutagenized DNAs isolated by sequencing to generate replicative form (RF) DNA. RF DNA is digested with EcoRI and ApaLI and these fragments are exchanged for wild type segments in the gB expression plasmid pXgB23 (see below), or in a similar gB construct where transcription is promoted by the murine CMV immediate early promoter.

An expression vector, pCMVAdhfr, employing the human CMV major immediate early (MIE) promoter and also containing the mouse dhfr cDNA linked to the adenovirus major late promoter (Stuve, et al. (1987) *J Virol* 61:326–335), was used to clone a 2196 bp EagI/XhoI gB fragment as a BamHI/XhoI fragment taken from pXgB9. This gB construct, pXgB23, has an insert identical at the 5' end to the gB insert of pXgB12 and pXgB13 in that it contains 153 bp of 5'-untranslated gB leader sequence. The construct is identical at the 3'end to the gB insert of pXgB8 in that it is truncated at the C-terminus by the deletion of amino acids 681–907 removing the transmembrane domain and C-terminal domains.

All bacterial cloning was done in Escherichia coli HB101 or DH5alpha according to the procedure of Spaete et al., (1985b) *J Virol* 54:817–824. Procedures used for preparation of plasmid DNA and restriction enzyme analyses are also described in Spaete et al., 1985b, *supra*. All plasmids used in transfections were banded twice in cesium chloride gradients. Restriction enzymes and T4 DNA ligase were purchased from New England Biolabs or Bethesda Research Laboratories (BRL) and were used according to the manufacturer's specifications.

Nucleotide Sequence Determination and Analysis. DNA fragments were subcloned into M13 phage vectors mp18 and mp119 (Pharmacia, Piscataway, N.J.) as well as polylinker derivatives of these vectors, plasmids rt1 and rt2. Plasmid rt1 contains a polylinker with the following restriction enzyme sites in the order given: HindIII, XbaI, EcoRV, SalI, SphI, BamHI, NcoI, PstI, KpnI, SstI, EcoRI. In rt2 the site order in the polylinker is reversed. Single-stranded viral DNA was generated as template for sequencing by the dideoxy nucleotide chain-termination method of Sanger, F., et al. (1977) *Proc Natl Acad Sci USA* 74:5463–5467. The dGTP base analog, 7-deaza dGTP (American Bionetics, Hayward, Calif.; Boehringer Mannheim Biochemicals), was used to resolve compressed regions (regions with high G/C content). The DNA was sequenced in its entirety on both strands and all junctions were bridged using oligonucleotide primers synthesized on an Applied Biosystems 380A synthesizer.

DNA Transfections. COS-7 cells (Gluzman, Y. (1981) *Cell* 23:175–182)-were transfected as described by Spaete et al., 1985. Briefly, 10 to 35 ug of plasmid DNA was mixed with 1.4 ml DME-50 mM Tris hydrochloride (pH 7.4) containing 400–600 ug of DEAE dextran per ml and added to 6 cm dishes containing cells at 50–80% confluency. Cells were washed with DME-50 mM Tris hydrochloride (pH 7.4) at 4–6 h posttransfection and incubated in DME-10% FCS at 37° C. After 24 hr, a portion of the transfected cells were subcultured into 4-chamber plastic slide wells (Lab-Tek) for immunofluorescence studies. Other dishes of cells were allowed to grow to confluence and conditioned media was harvested at 72 hr posttransfection.

A DHFR-deficient CHO cell line (Urlaub and Chasin (1980) *Proc Natl Acad Sci USA* 77:4216–4220) was cotransfected as described in Stuve, et al., *supra*, using plasmids pXgB8 and Ad-dhfr. Selective medium, consisting of DME with 10% dialyzed fetal calf serum and supplemented as described in Pachl, et al. (1987) *J Virol* 61:315–325), was applied to the transfected cells at 2 days post-infection. Several dhfr positive clones were analyzed for gB expression by immunofluorescence and ELISA of conditioned media. Stable cell lines secreting gB were examined and the highest producing clone expressed gB at a level similar to that detected in COS cells.

It is also possible to increase gB expression on these stable cell lines using methotrexate (MTX) amplification as taught in the art.

Immunofluorescence. COS-7 cells producing gB were identified by indirect immunofluorescence using the murine monoclonal 15D8 (Rasmussen et al., 1985) as the primary antibody and FITC-conjugated goat anti-mouse IgG (Tago, Inc., Burlingame, Calif.; Chemicon, El Segundo, Calif.) as the secondary antibody. The FITC conjugates were used at dilutions of 1:50 (Tago) and 1:80 (Chemicon). Slides were observed using a Leitz Dialux 20 EB fluorescent microscope.

Expression of gB was detected by 15D8 in COS cells transfected with all four gB expression plasmids, indicating that the p130 and p55 glycoproteins are encoded by the gB gene. Transfected cells which received truncated versions of gB exhibited a diffuse cytoplasmic immunofluorescent staining pattern. In contrast, cells transfected with the full length gB gene showed a punctate cytoplasmic staining pattern, which suggests a membrane association due to the presence of the transmembrane domain in these constructs.

ELISA Assay for gB. Microtiter plates (Immulon 1, Dynatech Laboratories, Inc.) were coated with murine monoclonal 15D8 gamma globulin (0.1 ug/well) diluted in 50 mM sodium borate (pH 9.1) and incubated for 2 hr at 37° C. The plates were washed, incubated for 1 hr with phosphate-buffered saline (PBS; 0.15 M NaCl, 2.7 mM KCl, 15.3 mM $Na_2HPO_4$, 1.5 mM $KH_2PO_4$) plus 2.0% BSA and then incubated overnight at 37 ° C. with conditioned media from transfected COS cells or a mixture of CMV glycoproteins (described below) which included gB. Washed plates were then incubated for 1 hour at 37° C. with a human anti-CMV serum (Whitaker M. A. Bioproducts, Inc.), followed by incubation for 1 hour at 37° C. with a 1:500 dilution of peroxidase-conjugated goat anti-human IgG (Cooper Biomedical, Inc.). The plates were developed with 0.83 mg/ml O-phenylenediamine in 0.1 M citrate-phosphate buffer (pH 5.0) plus 0.015% $H_2O_2$, the reaction stopped with 4 M $H_2SO_4$, and the absorbance read at 490 nm. After each incubation with antigen or antibodies, the plates were washed 5 times with PBS plus 0.05% Tween 20 and 0.1% BSA and 5 times with PBS alone for the final wash. All dilutions of antigens and antibodies were made in PBS plus 0.05% Tween 20 and 0.5% BSA.

The CMV glycoprotein mixture used as a standard for the ELISA was prepared by infecting approximately $4 \times 10^8$ HF cells with CMV (Towne) at a MOI of 0.2. Seven days after infection, the cells were lysed in 40 ml of lysis buffer (LB) containing 150 mM NaCl, 20 mM Tris pH 7.5, 1% NP40, 0.5% DOC, 1 mM PMSF, 1 ug/ml pepstatin and 17 ug/ml aprotinin. The lysate was passed over a column of lentil lectin Sepharose-4B (Sigma Chemical Co., St. Louis, Mo.) equilibrated in LB. The column was washed in LB plus 0.5 M NaCl and bound glycoproteins eluted in LB plus 0.5 M NaCl and 1.0 M alpha-methylmannoside.

Conditioned media was collected from the transfected cells containing the truncated gB gene and analyzed for the presence of secreted gB protein by the indirect ELISA specific for CMV gB. As expected, gB protein was detected in media taken from cells expressing the truncated version (pXgB7 and pXgB8) of the protein as provided by the data in Table 1 below.

TABLE 1

Expression of Truncated gB in COS-7 Cells[a]

| Plasmid | Relative Absorbance Values | Fold Enhancement |
|---|---|---|
| pSV7d | 0.03 | — |
| pXgB7 | 0.17 | 5.7 |
| pXgB8 | 1.04 | 34.7 |

[a]COS-7 cells were transfected with CMV gB expression plasmids and at 72 h posttransfection conditioned medium was collected and the presence of gB was determined by ELISA using the mouse monoclonal 15D8. The absorbance values were taken from the average of two determinations of equivalent dilutions which were within the linear portion of a standard curve. The standard curve was derived using a mixture of lentil lectin purified CMV glycoproteips, which included gB, isolated from infected cells.

Proteolytic Cleavage Inhibition Studies. Both cleaved (93 kDa and 31 kDa) and uncleaved (110 kDa) forms of gB are secreted from a CHO cell line (line 67.77) transformed with plasmid pXgB8. Cell line 67.77, expressing a truncated secreted form of gB and negative cell line 5—5, were radiolabeled with $^{35}$S-methionine for 2 h in DME medium or REM (reinforced Eagle's medium) lacking calcium with or without the addition of the calcium-specific ionophore A23187 at increasing concentrations (0.062 uM to 0.25 uM). The cells were chased with unlabeled media for 4 h, lysates and media were immunoprecipitated with MAb 15D8, subjected to 12% SDS-PAGE and autoradiographed. The dose of A23187 which most completely inhibits gB cleavage is 0.25 uM. The results clearly indicate that the 93 kDa and 31 kDa gB cleavage fragments were chased into the 110 kDa precursor with increasing drug concentration, however cleavage of the precursor was not completely inhibited.

These results indicate that (i) the 110 kDa precursor observed by radioimmunoprecipitation and Western blot analysis does represent inefficiently cleaved precursor and not an unreduced complex of cleavage products; (ii) the uncleaved precursor is recognized by the conformation dependent virus neutralizing MAb 15D8 demonstrating that the native structure of this important epitope is maintained in the 110 kDa molecule; and (iii) the ability to chase the 93 kDa and 31 kDa cleavage products into the 110 kDa precursor with increasing concentrations of drug establishes the precursor/product relationship of these fragments and demonstrates that the 93 kDa fragment represents the N-terminus of gB. The identity of the 31 kD molecules as the C-terminal fragment is established by amino acid sequence analysis and is described below. Since an uncleaved gB molecule will be simpler to purify from CHO conditioned media as compared to the partially cleaved complex currently being purified from CHO cell line 67.77, a proteolytic cleavage site gB mutant facilitates the isolation and purification of this important molecule.

N-terminal Amino Acid Sequence of gp55 and Determination of the gp55 Cleavage Site in gB. Glycoprotein B was purified by passing clarified cell lysate from CMV-infected human foreskin fibroblasts over an immunoaffinity column prepared with monoclonal antibody 15D8. The proteins bound to the column were eluted with ammonium thiocyanate and concentrated by precipitation with trichloroacetic acid. The proteins were then separated on a 10% preparative SDS-polyacrylamide gel, followed by electrophoretic transfer of the proteins onto an Immobilon membrane (Millipore). The membrane was stained with Coomassie blue to locate the transferred proteins. The gp55 band was excised and used for sequence determination by Edman degradation using a gas phase protein sequencer (Applied Biosystems, Foster City, Calif.). Phenylthiohydantoin (PTH) residues were identified by C18 reverse-phase high-pressure liquid chromatography.

The resulting sequence analysis of the amino acids at the N-terminus of gp55 is shown in Table 2 and localizes the cleavage site to the peptide bond following the dibasic residues $Lys_{459}$ $Arg_{460}$. The cleavage site is shown on FIG. 2 as a bold arrow directed between $Arg_{460}$ and $Ser_{461}$.

TABLE 2

Sequence analysis of amino acids at the N-terminus of gp55

| Cycle | Predicted Residue[a] | Observed Residue | Yield (pmol)[b] |
|---|---|---|---|
| 1 | S | S | 68 |
| 2 | T | T | 54 |
| 3 | D | D | 63 |
| 4 | G | G | 75 |
| 5 | N | N | 50 |
| 6 | N | N | 20c |
| 7 | A | A | 68 |
| 8 | T | T | 29 |
| 9 | H | H | 11 |
| 10 | L | L | 85 |

[a]The amino acid sequences are based on nucleotide sequences from the Towne strain of CMV (see FIG. 2). [b]Picomoles of phenylthiohydantoin (PTH) amino acid uncorrected for background or lag. [c]The low yield of PTH-asparagine may indicate the presence of glycosylation at this site.

Deletion Mapping of the gB Neutralizing Epitope Recognized by Monoclonal 15D8. The truncated version of the gB gene encoded by pXgB7 was used to generate additional C-terminal deletions in the gp55 region of gB. A deletion plasmid, pXgB16, which eliminated 34 amino acids was generated by removing a 102 bp SalI/XhoI fragment encompassing amino acids 647–680. This DNA fragment was 5' proximal to the XhoI site used in the construction of pXgB7. A second deletion plasmid, pXgB17, deleted a 186 bp BglII/XhoI fragment encoding 62 amino acids which encompassed amino acids 619–680. Thus, pXgB16 and gXgB17 express processed/truncated proteins of 186 amino acids (residues $Ser_{461}$ to $Asp_{646}$) and 158 amino acids (residues $Ser_{461}$ to $Ile_{618}$) respectively.

A third deletion plasmid, pXgB18, eliminated 369 amino acids and was generated by removing a 1106 bp fragment encompassing amino acids 43–411 from pXgB8. The gB insert is identical to that described for pXgB22.

The ability to detect expression of these truncated constructs was analyzed after transient expression in COS-7 cells by ELISA using monoclonal 15D8 as a probe as described above. As shown in Table 3, expression was detected in media conditioned by cells transfected with pXgB7 as expected from earlier results. Expression was also detected in media conditioned by the cells transfected with pXgB16 expressing the 186 amino acid truncated gp55 fragment and with pXgB18 expressing the 287 amino acid gB fragment not counting the cleaved signal peptide. Expression was not detected in media from cells receiving the control plasmid, pSV7d, or from cells receiving pxgB17 which should express the 158 amino acid gp55 fragment. However, expression from pXgB18 was detected by immunofluorescence of transfected COS cells, indicating that 15D8 could recognize this N-terminal truncated construct. These results indicate that the 15D8 epitope maps within the 186 amino acid gp55 fragment encoded by pXgB16 and by pXgB18, and further that deletion of an additional 28 amino acids from the C-terminus of this fragment must remove a portion of the epitope essential for reactivity with 15D8.

TABLE 3

Mapping of the gB Neutralizing Epitope[a]

| Plasmid | Relative Absorbance Values | Expression |
|---|---|---|
| pSV7d | 0.00 | − |
| pXgB7 | 0.24 | + |
| pXgB16 | 0.08 | + |
| pXgB17 | 0.00 | − |
| pXgB18 | 0.00 | +[b] |

[a]See Table 1, footnote a.
[b]Measured by immunofluorescence.

Additional experiments were run using the truncated gB products to determine whether a panel of monoclonal antibodies produced against a family of CMV glycoproteins, previously designated gA1–gA6 (U.S. Pat. No. 4,689,225), reacted with the proteins expressed by the plasmids described above.

Transient expression experiments with COS cells transfected with plasmid encoding sequences as described for pXgB17, which lacks 289 carboxyl-terminal amino acids of gB, showed immunofluorescent reactivity of this gB truncated derivative with 10 independently derived monoclonal antibodies (see FIG. 4 and Banks et al. (1989) *J Gen Virol* (In press)). Eight of the reactive antibodies neutralized virus in the presence of complement, whereas one did not require complement for neutralization.

It was also determined that 12 additional antibodies reacted with a stable cell line producing a gB derivative (pxgB8) lacking 227 carboxyl-terminal amino acids of gB.

These results establish both the identity and location of neutralizing domains of the gB molecule and confirm the virus neutralizing characteristics of the gB truncated proteins described herein.

Modifications of the above-described modes for carrying out the invention that are obvious to those of skill in the technical fields related to the invention are intended to be within the scope of the following claims.

What is claimed is:

1. A DNA hybridization assay for detecting CMV homologous DNA sequences in a biological specimen comprising:

(a) incubating a biological sample with a DNA probe under conditions that result in hybridization of the DNA probe to a gp55 nucleotide sequence but not to other nucleotide sequences within the biological sample, wherein said DNA probe comprises a single nucleic acid of about 8 to about 20 nucleotides complementary to the gp55 nucleotide sequence; and (b) detecting the DNA duplexes containing the DNA probe.

2. The DNA hybridization assay of claim 1 wherein said DNA probe is labeled, and the presence of the gp55 nucleotide sequence within the biological sample is detected by the presence of the label.

3. The DNA hybridization assay of claim 1 wherein said DNA probe consists of about 8 to about 20 nucleotides complementary to the gp55 nucleotide sequence.

* * * * *